United States Patent
Endou et al.

(10) Patent No.: US 7,307,145 B2
(45) Date of Patent: Dec. 11, 2007

(54) SODIUM-INDEPENDENT TRANSPORTER TRANSPORTING SMALL-SIZED NEUTRAL AMINO ACID, GENE THEREOF AND METHOD OF ANALYZING TRANSPORTER FUNCTION BY CONSTRUCTING FUSED PROTEINS ENABLING THE SPECIFICATION OF THE FUNCTION

(75) Inventors: Hitoshi Endou, Sagamihara (JP); Yoshikatsu Kanai, Hachioji (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/490,824

(22) PCT Filed: Sep. 30, 2002

(86) PCT No.: PCT/JP02/10143

§ 371 (c)(1),
(2), (4) Date: Sep. 22, 2004

(87) PCT Pub. No.: WO03/029466

PCT Pub. Date: Apr. 10, 2003

(65) Prior Publication Data

US 2005/0282160 A1    Dec. 22, 2005

(30) Foreign Application Priority Data

Sep. 28, 2001 (JP) ............................. 2001-304506
Oct. 5, 2001  (JP) ............................. 2001-310585

(51) Int. Cl.
*C07K 14/705* (2006.01)
*C12N 15/12* (2006.01)
*C12N 15/62* (2006.01)

(52) U.S. Cl. .................... 530/350; 435/69.1; 435/69.7; 435/252.3; 435/320.1; 536/23.4; 536/23.5

(58) Field of Classification Search ...................... None
See application file for complete search history.

(56) References Cited

FOREIGN PATENT DOCUMENTS

| JP | 2000-342270 | 12/2000 |
| JP | 2001-46070 | 2/2001 |
| WO | WO 00/14228 | 3/2000 |
| WO | WO 01/58944 | 8/2001 |

OTHER PUBLICATIONS

A. Chairoungdua et al., *The Journal of Biological Chemistry*, 276(52):49390-49399 (2001).
M. Palacin, *J. Exp. Biol.*, 196:123-137 (1994).
R. Pfeiffer et al., *Mol. Biol. Cell.*, 10(12):4135-4147 (1999).
Database EMBL, "Mus Musculus 0 Day Neonate Kidney cDNA, RIKEN full-length enriched library, clone: D630003H08, 3' end partial sequence", XP002313135 (Jul. 19, 2000).
Database EMBL, "um30a03.x1 sugano mouse kidney mkia Mus musculus cDNA clone IMAGE: 2236012 3'similar to WP:Y53H1C.B CE22438; mRNA sequence", XP002313136 (Oct. 21, 1999).
Chairoungdua A. et al. "Identification and characterization of a novel member of the heterodimeric amino acid transporter family presumed to be associated with an unknown heavy chain" Journal of Biological Chemisty, American Society of Biological Chemists, Baltimore, MD, US, vol. 276, No. 52, Dec. 2001, pp. 49390-49399, XP002960766, ISSN: 0021-9258.
Chairoungdua A. et al. "Identification of an amino acid transporter associated with the cystinuria-related type II membrane glycoprotein" Journal of Biological Chemistry, American Society of Biological Chemists, Baltimore, MD, US, vol. 274, No. 41, Oct. 8, 1999, pp. 28845-28848, XP002941606, ISSN: 0021-9258.
Segawa H. et al. "Identification and functional characterization of a NA+-independent neutral amino acid transporter with broad substrate selectivity" Journal of Biological Chemistry, American Society of Biological Chemists, Baltimore, MD, US, vol. 274, No. 28, Jul. 9, 1999, pp. 19745-19751, XP002293829, ISSN: 0021-9258.
H. Segawa et al., "Cloning, functional expression and dietary regulation of the mouse neutral and basic amino acid transporter (NBAT)", Biochem, J., vol. 328, pp. 657-664 (1997).
Y. Kanai et al., "Expression Cloning and Characterization of a Transporter for Large Neutral Amino Acids Activated by the Heavy Chain of 4F2 Antigen (CD98)", J. Biol. Chem., vol. 273, No. 37, pp. 23629-23632 (1998).

*Primary Examiner*—John Ulm
(74) *Attorney, Agent, or Firm*—Peter F. Corless; Christine C. O'Day; Edwards Angell Palmer & Dodge LLP

(57) ABSTRACT

The invention provides a sodium independent transporter which transports a small-sized neutral amino acid and its analog; its gene; fused proteins; and a method of analyzing the function of the transporter. Further provided is a use for the transporters as described by the invention.

12 Claims, 15 Drawing Sheets

FIG. 1

Asc-2          rBAT
               4F2hc

Asc-2-rBAT fusion protein

| Asc-2 | | rBAT |
|---|---|---|
| CAG AAA AAT | ACT AGT GAA TTC | GAT GAG GAC |
| Q   K   N   | T   S   E   F   | D   E   D   |

Asc-2-4F2hc fusion protein

| Asc-2 | | 4F2hc |
|---|---|---|
| CAG AAA AAT | ATC GAT | AGC CAG GAC |
| Q   K   N   | I   D   | S   Q   D   |

SODIUM-INDEPENDENT TRANSPORTER TRANSPORTING SMALL-SIZED NEUTRAL AMINO ACID, GENE THEREOF AND METHOD OF ANALYZING TRANSPORTER FUNCTION BY CONSTRUCTING FUSED PROTEINS ENABLING THE SPECIFICATION OF THE FUNCTION

TECHNICAL FIELD

The present invention relates to a protein associated with the sodium-independent transport of a small-sized neutral amino acid and its analogue, a fusion protein thereof, as well as a gene encoding said protein. The invention also relates a method for controlling the cell proliferation or for altering the in vivo pharmacokinetics of a pharmaceutical, toxic substance or exogenous foreign body by modulating an ability to transport a small-sized neutral amino acid and its analogue possessed by a protein associated with the sodium-independent transport of a small-sized neutral amino acid and its analogue, by means of employing said protein, its fusion protein, its specific antibody, or its function-promoting substance or function-suppressing substance, as well as an agent for controlling an ability to transport a small-sized neutral amino acid and its analogue comprising said substances.

Furthermore, the invention relates to a method for analyzing a function of a transporter comprising a step for allowing a transporter protein, whose function can not be identified because of the inability to be transferred to a cell membrane in an exogenous gene expression system, to be transferred to the cell membrane by forming a fusion protein with a protein which promotes the transfer to the cell membrane.

BACKGROUND ART

A cell always requires the uptake of an amino acid as a nutrition, and such a function is exerted by an amino acid transporter which is a membrane protein present in a cell membrane. The amino acid transporter is located in a certain position in each tissue in a multicellular organism and plays an important role in the expression of a specific function of each tissue.

A transport system asc is an amino acid transport system which transports small-sized neutral amino acids such as alanine, serine and cysteine, and was reported originally with regard to an erythrocyte membrane. Thereafter, it was identified also in a cultured cell [Christensen, Physiol. Rev. Vol. 70, page 43, 1990]. The transport system asc is a transporter which is independent of sodium, i.e., whose function requires no sodium ion. Its transport substrate selectivity and transport profile are known to vary somewhat depending on cells and animal species.

While the transport system asc exhibits a high affinity to a transport substrate such as alanine, serine and cysteine, an analogous transport system is known to exist which is a transport system C whose transport substrates are also small-sized neutral amino acids such as alanine, serine and cysteine but which exhibits a lower affinity to the transport substrate [Young et al., Biochem. J. Vol. 154, page 43, 1976; Young et al., Biochem. J. Vol. 162, page 33, 1977]. The transport system C is considered to be a subclass of the transport system asc. A sheep having a genetic defect of the transport system C was identified, and its erythrocyte was found to have a reduced glutathion content, revealing the importance of the cysteine uptake via a cell membrane in the glutathion production [Young et al., Nature, Vol. 254, page 156, 1975].

However, a conventional method involves a difficulty in analyzing the details of the transport of an amino acid or its analogue via the amino acid transport system asc and the in vivo functional roles, and it has been desired to enable a detailed functional analysis by isolating a gene of a neutral amino acid transporter responsible for the function of the amino acid transport system asc.

As small-sized neutral amino acid transporters, ASCT1 and ASCT2 have been cloned [Kanai, Curr. Opin. Cell Biol., Vol. 9, page 565, 1997]. Nevertheless, they are sodium-dependent transporters, and are different in principle from the sodium-independent amino acid transport system asc. Further, a glycine transporter and a proline transporter have also been cloned, however, each transports only glycine or proline in a sodium-dependent manner, unlike to the transport system asc [Amara and Kuhar, Annu. Rev. Neurosci., Vol. 16, page 73, 1993].

The cDNAs of rBAT and 4F2hc, i.e., type II membrane glycoproteins each having only a single membrane-spanning structure which are not the transporters themselves but are considered to be amino acid transporter-activating factors, have been cloned, and are known to activate the uptake of basic amino acids together with neutral amino acids when being expressed in an oocyte of a xenopus [Palacin, J. Exp. Biol., Vol. 196, 123, 1994].

As a transporter which transports neutral amino acids selectively, neutral amino acid transporters corresponding to the transport system L, i.e., LAT1 [Kanai et al., J. Biol., Chem., Vo. 273, page 23629 to 23632, 1998] and LAT2 [Segawa et al., J. Biol. Chem, Vol. 274, page 19745 to 19751, 1999] have been cloned. It was also revealed that the LAT1 and the LAT2 are capable of exerting their functions only when being coexisting with a cofactor 4F2hc which is a single-membrane-spanning type protein. The both are independent of $Na^+$, and the LAT1 exhibits an exchange transport activity serving to transport large-sized neutral amino acids such as leucine, isoleucine, valine, phenylalanine, tyrosine, tryptophan, methionine and histidine, while the LAT2 exhibits a wide substrate selectivity serving to transport small-sized neutral amino acids such as glycine, alanine, serine, cysteine and threonine in addition to the large-sized neutral amino acids. Nevertheless, their substrate selectivity is also different from that of the amino acid transport system asc.

As proteins analogous to the neutral amino acid transporters LAT1 and LAT2, $y^+$LAT1 and $y^+$LAT2 having the functions of a transport system $y^+$L which transports neutral amino acids and basic amino acids have been cloned [Torrents et al., J. Biol. Chem., Vol. 273, page 32437 to 32445, 1998]. It was also revealed that both of $y^+$LAT1 and $y^+$LAT2 are capable of exerting their functions only when being coexisting with a cofactor 4F2hc. The $y^+$LAT1 and $y^+$LAT2 transport mainly glutamine, leucine and isoleucine as neutral amino acids, exhibiting the substrate selectivity different from that of the amino acid transport system asc.

As a transporter requiring the cofactor 4F2hc for exerting its function, xCT which is a protein analogous to the neutral amino acid transporters LAT1 and LAT2 has been cloned [Sato et al., J. Biol. Chem., 274: 11455-11458, 1999]. The xCT transports cystine and glutamic acid, exhibiting the substrate selectivity different from that of the amino acid transport system asc.

Further, as a transporter requiring another cofactor rBAT having a structure analogous to that of 4F2hc, BAT1 which is a protein analogous to the neutral amino acid transporters LAT1 and LAT2 has been cloned [Chairoungdua et al., J. Biol. Chem. 274: 28845-28848, 1999]. The BAT1 transports cystine, neutral amino acids and basic amino acids, exhibiting the substrate selectivity different from that of the amino acid transport system asc.

As described above, a molecular entity of a transporter which functions as a result of the binding to the 4F2hc and the rBAT was characterized and it was revealed that there is a group of the transporters exerting the transporting ability by forming a molecular complex with a type II glycoprotein.

Moreover, as a transporter requiring the cofactor 4F2hc for expressing a function, Asc-1 which is a protein analogous to the neutral amino acid transporters LAT1 and LAT2 has been cloned [Fukasawa et al., Biol. Chem. 275: 9690-9698, 2000]. The Asc-1 transports alanine, serine, cysteine, threonine, glycine and the like selectively, exhibits the substrate selectivity of the amino acid transport system asc, and was proven to be the first isoform of the transporting system asc.

The Asc-1 exhibits a property different from that of a traditional transporting system asc reported with regard to the erythrocyte membrane, since it transports not only L-amino acids but also D-forms of alanine, serine, cysteine and threonine, α-aminoisobutyric acid and β-alanine. Accordingly, it was believed that there is a transporter, other than the Asc-1, corresponding to the traditional transporting system asc.

In an attempt to prepare a fusion protein of a transporter with another protein, $b^{0,+}AT$ was combined with a single-membrane-spanning type cofactor, rBAT, for its transfer to a cell membrane [Pfeiffer et al., Mol. Biol. Cell. 10: 4135-4147, 1999]. Nevertheless, this fusion protein is the one prepared in accordance with an authentic combination of the $b^{0,+}AT$ and the rBAT, and is not intended to allow a transporter protein, which can not be expressed in the cell membrane because of the absence of cofactor, to be expressed forcibly on the cell membrane for the purpose of identifying its functions.

DISCLOSURE OF THE INVENTION

An objective of the invention is to provide a gene of a transporter which transports small-sized neutral amino acids in a sodium-independent manner and exhibits the functions of a traditional transport system asc reported with regard to the erythrocyte membrane as well as a sodium-independent small-sized neutral amino acid transporter which is a polypeptide encoded by said gene. Also by means of producing a fusion protein with this transporter, the invention provides a method for analyzing a function of a transporter protein whose function can not be identified because of the inability to be transferred to a cell membrane in an exogenous gene expression system.

Other objectives will be known readily from the following description.

BRIEF DESCRIPTION OF THE DRAWINGS

FIG. 1 shows the amino acid sequences of mouse Asc-2 (SEQ ID NO: 1) and mouse Asc-1 (SEQ ID NO: 7), rat LAT1 (SEQ ID NO: 8), rat y+LAT1 (SEQ ID NO: 9), mouse xCT (SEQ ID NO: 10) and rat BAT1 (SEQ ID NO: 11) for comparison with each other. Twelve assumed membrane-spanning sites are designated with lines. A conserved cystine residue is designated with a *, and an assumed cAMP-dependent phosphorylation site with #.

In FIG. 13, the indication (−) means no addition, AIB means α-aminoisobutyric acid, MeAIB means α-methylaminoisobutyric acid, GABA means γ-aminobutyric acid and BCH means 2-amino-2-norbornanecarboxylic acid. The ordinate indicate a ratio of the uptake level with the value of (−) being regarded as 100%.

In FIG. 15, the designation C means a renal cortex, OM means a renal medulla outer layer, and IM means a renal medulla inner layer.

BEST MODE FOR CARRYING OUT THE INVENTION

Figure 2:
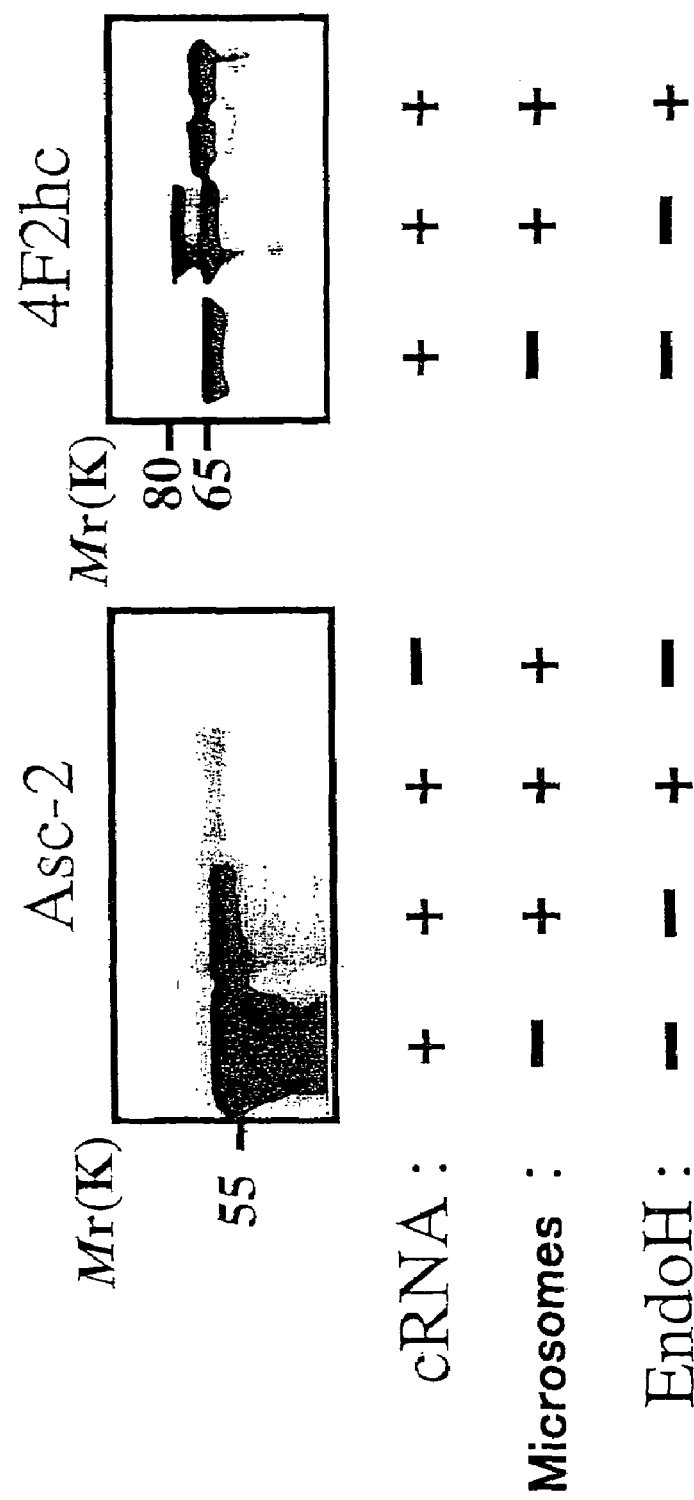
FIG. 2 is a photograph substituted for the drawing showing the results of the in vitro translation of the Asc-2 (left) and the mouse 4F2hc (right). In the in vitro translation of the Asc-2 (left), a 55 kDa band was observed, revealing that no sugar was added in the presence of a canine pancreas microsome fraction (Microsomes) and the band size was not changed by a saccharide chain decomposition enzyme endoglycosidase (EndoH). On the contrary, the in vitro translation of the 4F2hc (right) exhibited a 65 kDa band, and a 80 kDa band was observed in the presence of canine pancreas microsome fraction. This band was reverted to a 65 kDa band by the saccharide chain digestion enzyme endoglycosidase H.

The present inventors searched an EST (expressed sequence tag) database using the base sequence of the translation region of the cDNA of a LAT1 and identified a base sequence analogous to the LAT1. The base sequence of the corresponding cDNA clone was determined and was proven to encode a novel protein. In addition, a fusion protein of a translation product of this gene with a 4F2hc or rBAT was prepared, and expressed on a cell membrane of an oocyte of a *Xenopus*. As a result, the function of the translation product of this gene was proven to correspond to a neutral amino acid transport system asc and, unlike to an already known Asc-1, also correspond to a traditional transport system asc which has previously been reported with regard to an erythrocyte membrane, whereby the invention was established.

Thus, the invention is a protein selected from the group consisting of the following (A) and (B):
(A) a protein consisting of the amino acid sequence represented by SEQ ID NO.1; and,
(B) a protein having an ability to transport a small-sized neutral amino acid and its analogue in a sodium-independent manner which consists of an amino acid sequence formed as a result of the deletion, substitution or addition of one or more amino acids in the amino acid sequence represented by SEQ ID NO.1.

Also the invention is a gene consisting of a DNA selected from the group consisting of the following (a) and (b):
(a) a DNA consisting of the base sequence represented by SEQ ID NO.2; and,
(b) a DNA encoding a protein having an ability to transport a small-sized neutral amino acid and its analogue in a sodium-independent manner which hybridizes under a stringent condition with a DNA consisting of the base sequence represented by SEQ ID NO.2.

Also the invention is a method for analyzing a function of a transporter protein by allowing the transporter protein, whose function can not be identified because of the inability to be transferred to a cell membrane in an exogenous gene expression system, to be transferred to the cell membrane by converting said protein into a fusion protein with a protein having the amino acid sequence represented by SEQ ID NO.3 (4F2hc) or a protein having the amino acid sequence represented by SEQ ID NO.5 (rBAT).

A novel protein having an ability to transport a small-sized neutral amino acid and its analogue in a sodium-independent manner, i.e., an amino acid transporter Asc-2

(asc-type amino acid transporter 2) can be converted into a fusion protein with the 4F2hc or rBAT whereby being expressed on a cell membrane and imparted with an ability to transport a small-sized neutral amino acid such as glycine, L-alanine, L-serine, L-cysteine and L-threonine with a high affinity. In addition, L-methionine, L-leucine, L-isoleucine, L-valine, L-phenylalanine, L-tyrosine, L-histidine, D-serine and D-alanine are also transported at a low affinity.

An inventive sodium-independent transporter Asc-2 which transports a small-sized neutral amino acid is expressed in vivo mainly in a kidney, placenta and skeletal muscle. A low expression is noted also in a spleen and lung.

SEQ ID NO.1 in the sequence listing described below represents the amino acid sequence of a mouse-derived sodium-independent transporter (mouse Asc-2) which transports a small-sized neutral amino acid, and SEQ ID NO.2 represents the full-length cDNA base sequence (about 1.8 kbp) of the respective gene together with the amino acid sequence (465 amino acids) of a protein encoded by the respective translation region.

As a result of the homology search of all sequences included in known DNA database (GenBank and EMBL) and protein database (NBRF and SWISS-PROT) for the amino acid sequence represented by SEQ ID NO.1 and the base sequence represented by SEQ ID NO.2, there are no identical sequences, suggesting that the sequences are novel.

A protein of the invention may, for example, be one having the amino acid sequence represented by SEQ ID NO.1 as well as a protein having an amino acid sequence formed as a result of the deletion, substitution or addition of one or more amino acids in the amino acid sequence represented by SEQ ID NO.1. The number of the amino acids undergoing the deletion, substitution or addition may be any as long as causing no loss of the neutral amino acid-transporting ability, and usually 1 to about 93, preferably 1 to about 47. Such a protein has an amino acid sequence homology usually of 1 to 80%, preferably 1 to 90% with the amino acid sequence represented by SEQ ID NO.1.

An inventive gene may, for example, be one having the base sequence represented by SEQ ID NO.2 as well as the one comprising a DNA which can hybridize under a stringent condition with a DNA consisting of the base sequence represented by SEQ ID NO.2. The DNA which can hybridize may be anyone as long as the protein encoded by the DNA has an ability to transport a neutral amino acid. Such a DNA has a base sequence homology usually of 70% or more, preferably 80% or more with the base sequence represented by SEQ ID NO.1. Such a DNA includes a naturally occurring variant gene, artificially modified variant gene, heterogeneous organism-derived homologous gene and the like.

In the invention, a hybridization under a stringent condition can be effected usually by conducting a hybridization for about 12 hours at a temperature of 37 to 42° C. in a hybridization solution whose salt concentration is 5×SSC or equivalent thereto followed by a preliminary washing if necessary with the solution whose salt concentration is 5×SSC or equivalent thereto, and by washing with the solution whose salt concentration is 1×SSC or equivalent thereto.

An inventive sodium-independent transporter gene transporting small-sized neutral amino acid can be isolated by conducting a screening using as a gene source a tissue or a cell of suitable mammalian animals. Mammalian animals may for example be non-human animals such as dog, cattle, horse, goat, sheep, monkey, pig, rabbit, rat and mouse, as well as human.

The gene screening and isolation can be conducted preferably by a homology cloning method and the like.

For example, a mouse or human kidney is employed as a gene source, from which an mRNA (poly(A)$^+$RNA) is prepared and used to construct a cDNA library, which is then screened using a probe corresponding to a LAT1-analogous sequence obtained by searching the EST (expressed sequence tag) data base (for example, GenBank™/EBI/DDBJ accession No. AI875555), whereby obtaining a clone containing an Asc-2 gene cDNA.

The base sequence of the resultant cDNA is determined by a standard method, and its translation region is analyzed to determine the protein encoded thereby, i.e., the amino acid sequence of the Asc-2.

Whether the resultant cDNA is a sodium-independent transporter gene transporting small-sized neutral amino acid or not, i.e., whether the gene product encoded by the cDNA is a sodium-independent transporter gene transporting small-sized neutral amino acid or not, can be verified for example as follows. Thus, based on the cDNA of the resultant Asc-2 gene, a cDNA encoding the fusion protein of the Asc-2 with a 4F2hc or rBAT is prepared and used to prepare an RNA complementary thereto (cRNA) (capped), which is introduced into and expressed in an oocyte. Then an ability to transport (take in) a neutral amino acid into the cell is verified by measuring the uptake of a substrate into the cell in accordance with a standard uptake test (Kanai and Hediger, Nature, Vol. 360, page 467-471, 1992) using a suitable neutral amino acid as a substrate.

An RNA complementary to the resultant Asc-2 gene cDNA is prepared and subjected to an in vitro translation method [Hediger et al., Biochim. Biophys. Acta, Vol. 1064, page 360, 1991] to synthesize an asc-1 protein, which is then examined for the size of the protein and the presence or absence of glycosylation by means of an electrophoresis.

Since the 4F2hc gene cDNA has already been reported [Fukasawa et al., Biol. Chem. 275: 9690-9698, 2000], this sequence data may be employed to obtain the 4F2hc gene easily for example by a PCR method.

SEQ ID NO.3 in the sequence listing described below represents the amino acid sequence (526 amino acids) of a mouse-derived 4F2hc, and SEQ ID NO.4 represents the full-length cDNA base sequence (about 1.8 kbp) of the respective gene together with the amino acid sequence of a protein encoded by the respective translation region.

Since the rBAT gene cDNA has also been reported [Segawa, H. et al., J. Biochem. J. 328: 657-664, 2000], this sequence data may be employed to obtain the rBAT gene easily for example by a PCR method.

SEQ ID NO.5 in the sequence listing described below represents the amino acid sequence (685 amino acids) of a mouse-derived rBAT, and SEQ ID NO.6 represents the full-length cDNA base sequence (about 2.3 kbp) of the respective gene together with the amino acid sequence of a protein encoded by the respective translation region.

A cDNA encoding the fusion protein of the Asc-2 with the 4F2hc or rBAT can readily be prepared for example by a PCR method based on the cDNA of the Asc-2 gene, cDNA of the 4F2hc gene or cDNA of the rBAT gene.

An expressing cell may be subjected to a similar uptake experiment to examine for a property of the Asc-2, such as a transport of the amino acids as a combination of the exchange transport type and a facilitated diffusion type as well as for the substrate selectivity and the pH dependency of the Asc-2.

Using the resultant Asc-2 gene cDNA, an appropriate cDNA library or genomic DNA library produced from a different gene source may be screened to isolate a homologous gene or chromosomal gene derived from a different tissue or different organism.

It is also possible to isolate the gene from a cDNA library or genomic DNA library by an ordinary PCR (polymerase chain reaction) method using a synthetic primer designed based on the disclosed data of the base sequence of an inventive gene (base sequence represented by SEQ ID NO.2 or its part).

A DNA library such as a cDNA library or genomic DNA library can be produced in accordance with the method described for example in Molecular Cloning (Sambrook, J., Fritsh, E. F. and Manitis, T., Cold Spring Harbor Press, 1989). Alternatively, a commercially available library, if any, may be employed.

An inventive sodium-independent transporter transporting small-sized neutral amino acid and its gene (Asc-2) can be produced for example by a gene recombination technology using a cDNA encoding it. For example, a DNA (such as cDNA) encoding the Asc-2 is integrated into a suitable expression vector, and the resultant recombinant DNA can be introduced into a suitable host cell. The expression system for producing a polypeptide (host-vector system) may for example be expression systems of bacteria, yeasts, insect cells and mammalian cells. Among these, the insect cells and the mammalian cells are preferred for the purpose of obtaining a functional protein.

A fusion protein of an inventive sodium-independent transporter transporting small-sized neutral amino acid and the 4F2hc or rBAT and their genes (Asc-2-4F2hc or Asc-2-rBAT) can be produced, for example, by a gene recombination technology using a cDNA encoding it. For example, a DNA (such as cDNA) encoding the Asc-2-4F2hc or Asc-2-rBAT is integrated into a suitable expression vector, and the resultant recombinant DNA can be introduced into a suitable host cell. The expression system for producing a polypeptide (host-vector system) may for example be expression systems of bacteria, yeasts, insect cells and mammalian cells. Among these, the insect cells and the mammalian cells are preferred for the purpose of obtaining a functional protein.

For example, to express a polypeptide in a mammalian cell, a DNA encoding an inventive sodium-independent transporter Asc-2 transporting small-sized neutral amino acid or a fusion protein of the Asc-2 with the 4F2hc or rBAT is inserted into the downstream of a suitable promoter (such as cytomegalovirus promoter, SV40 promoter, LTR promoter, elongation 1a promoter and the like) in a suitable expression vector (such as adenovirus vector, retrovirus vector, papilloma virus vector, vaccinia virus vector, SV40 vector, various plasmids and the like) to construct an expression vector. Then, with the resultant expression vector, a suitable animal cell is transformed to obtain a transformant which is then cultured in a suitable medium to allow the intended polypeptide to be produced. A mammalian cell serving as a host cell may for example be a cell line such as simian COS-7 cell, Chinese hamster CHO cell or human HeLa cell.

Accordingly, the invention provides a vector comprising an inventive gene described above or a gene encoding a protein in said gene, preferably an expression vector, as well as a host cell (transformant) which has been transformed with said vector.

A DNA encoding a sodium-independent transporter Asc-2 transporting small-sized neutral amino acid may for example be a cDNA having the base sequence represented by SEQ ID NO.1 as well as any DNA encoding the polypeptide designed based on the amino acid sequence without any limitation to the cDNA described above. In such a case, a codon encoding a single amino acid is known to present in 1-6 types respectively, any of which may be employed, and a sequence habing further higher expression efficiency can be designed while taking the frequency of the use of the codon by a host employed for the expression into consideration. A DNA having a designed base sequence can be obtained by a chemical synthesis of the DNA, fragmentation and binding of the cDNA described above, partial alteration of the base sequence and the like. The partial alteration of the base sequence or the introduction of a variation can be artificially accomplished by means of a site specific mutagenesis method [Mark, D. F. et al., Proceedings of National Academy of Sciences, Vol. 81, page 5662, (1984)] and the like utilizing the primers consisting of the synthetic oligonucleotides encoding the intended alteration.

A DNA encoding a fusion protein of a sodium-independent transporter Asc-2 transporting small-sized neutral amino acid with the 4F2hc or rBAT (Asc-2-4F2hc or Asc-2-rBAT) can be prepared for example by using a cDNA having the base sequence represented by SEQ ID NO.2 and the base sequence represented by SEQ ID NO.4 or the base sequence represented by SEQ ID NO.6, and it is also possible to use any DNA encoding the polypeptide designed based on the amino acid sequence without any limitation to the cDNA described above. In such a case, a codon encoding a single amino acid is known to present in 1-6 types respectively, any of which may be employed, and a sequence having further higher expression efficiency can be designed while taking the frequency of the use of the codon by a host employed for the expression into consideration. A DNA having a designed base sequence can be obtained by a chemical synthesis of the DNA, fragmentation and binding of the cDNA described above, partial alteration of the base sequence and the like. The partial alteration of the base sequence or the introduction of a variation can be artificially accomplished by means of a site specific mutagenesis method [Mark, D. F. et al., Proceedings of National Academy of Sciences, Vol. 81, page 5662, (1984)] and the like utilizing the primers consisting of the synthetic oligonucleotides encoding the intended alteration.

Accordingly, the invention provides a nucleotide comprising a partial sequence of consecutive 14 bases or more, preferably 20 bases or more, in the base sequence represented by SEQ ID NO.2 or a sequence complementary thereto.

An inventive nucleotide can be used as a probe for detecting a gene encoding a protein having an ability to transport a small-sized neutral amino acid and its analogue in a sodium-independent manner, and also as a primer in obtaining a gene encoding said protein or a gene encoding a protein highly homologous to said protein, and further can be used to modulate the expression of a gene encoding a protein having an ability to transport a small-sized neutral amino acid and its analogue in a sodium-independent manner for example by utilizing its antisense strand.

Using an inventive sodium-independent transporter transporting small-sized neutral amino acid or its immunologically equivalent polypeptide, its antibody can be obtained. The antibody can be utilized in detecting or purifying a sodium-independent transporter transporting small-sized neutral amino acid. The antibody can be produced by using as an antigen an inventive sodium-independent transporter transporting small-sized neutral amino acid, its fragment or synthetic peptide having its partial sequence. A polyclonal antibody can be produced by an ordinary method in which an antigen is inoculated into a host animal (such as rat and rabbit) and then an immune serum is recovered, while a monoclonal antibody can be produced by an ordinary hybridoma method.

Accordingly, the invention provides an antibody directed to a protein of the invention described above, preferably, a specific antibody directed to said protein.

An inventive protein has an ability to transport a small-sized neutral amino acid and its analogue in a sodium-independent manner, and such an ability is influenced potently by the presence of various substances. By screening for a substance inhibiting or promoting this ability, a control of the ability of the inventive protein to transport the substance becomes possible.

Accordingly, the invention provides a method for detecting an effect of a test substance serving as a substrate on an ability to transport a small-sized neutral amino acid and its analogue in a sodium-independent manner possessed by an inventive protein described above by means of employing said protein.

An amino acid transported by an inventive protein is a substance essential for the proliferation, growth and survival of a cell, and by controlling the uptake of such a substance into the cell, the proliferation and the growth of the cell can be controlled. Accordingly, the invention provides a method for controlling a cell proliferation by modulating an ability to transport a small-sized neutral amino acid and its analogue possessed by an inventive protein described above by means of employing said protein, its specific antibody, or its function-promoting substance or function-suppressing substance.

The gene of a fusion protein of an inventive sodium-independent transporter Asc-2 transporting small-sized neutral amino acid with the 4F2hc or rBAT and its expression cell can be used in an in vitro permeability test of a substance in the cell membrane where the Asc-2 is present or in a site where the Asc-2 is assumed to be present. The gene of a fusion protein of an inventive sodium-independent transporter Asc-2 transporting small-sized neutral amino acid with the 4F2hc or rBAT and its expression cell can be used also in developing a compound which permeates efficiently through the cell membrane where the Asc-2 is present or through a site where the Asc-2 is assumed to be present. Furthermore, the gene of a fusion protein of an inventive sodium-independent transporter Asc-2 transporting small-sized neutral amino acid with the 4F2hc or rBAT and its expression cell can be used in an in vitro inter-pharmaceutical interaction test in the cell membrane where the Asc-2 is present or in a site where the Asc-2 is assumed to be present.

Accordingly, the invention provides a method for altering the in vivo pharmacokinetics of a pharmaceutical, toxic substance or exogenous foreign body transported by an inventive protein described above by modulating an ability to transport a neutral amino acid and its analogue possessed by said protein by means of employing said protein, its specific antibody, or its function-promoting substance or function-suppressing substance.

Since an inventive protein has an ability to transport a small-sized neutral amino acid and its analogue in a sodium-independent manner and this ability can be suppressed not only by the number of the proteins present in a cell but also by the presence of various substances (in the presence of such as function-suppressing substance) and can also be promoted (in the presence of such as function-promoting substance) as described above, the invention provides an agent for controlling an ability to transport a small-sized neutral amino acid and its analogue possessed by an inventive protein described above which comprises said protein, its specific antibody or its function-promoting substance or function-suppressing substance.

An inventive transporting ability-controlling agent can be used as a cell proliferation-controlling agent because of its ability to control the proliferation and the growth of a cell and also as an agent for controlling the in vivo pharmacokinetics of a pharmaceutical, toxic substance or xenobiotics because of its ability to modulate and control the in vivo pharmacokinetics of the pharmaceutical, toxic substance or xenobiotics.

By suppressing an inventive sodium-independent transporter Asc-2 transporting small-sized neutral amino acid, the permeation of a certain compound through the cell membrane where the Asc-2 is expressed or through a site where the Asc-2 is assumed to be present can be suppressed. Furthermore, the gene of a fusion protein of an inventive sodium-independent transporter Asc-2 transporting small-sized neutral amino acid with the 4F2hc or rBAT and its expression cell can be used in developing a pharmaceutical which suppresses the permeation of a compound transported by the Asc-2 through the cell membrane and also the permeation through the site where the Asc-2 is assumed to be present (Asc-2-specific inhibitor and the like).

Accordingly, the invention also provides a method for analyzing a function of a transporter protein comprising a step for allowing a protein, whose function can not be identified because of the inability to be transferred to a cell membrane in an exogenous gene expression system, to be transferred to the cell membrane by converting said protein into a fusion protein with a protein which promotes the transfer to the cell membrane. An inventive protein which promotes the transfer to the cell membrane is preferably a protein having the amino acid sequence represented by SEQ ID NO.3 or 5 or a protein consisting of an amino acid sequence formed as a result of the deletion, substitution or addition of one or more amino acids in said protein. A protein whose function can not be identified because of the inability to be transferred to a cell membrane in an exogenous gene expression system is preferably but not limited to a transporter protein.

The inventors also found that a protein having an amino acid sequence represented by SEQ ID NO.3 or NO.5 has an ability to promote the transfer of a protein into a cell membrane, and accordingly the invention also provides an agent for promoting the transfer of a protein into a cell membrane comprising a protein having an amino acid sequence represented by SEQ ID NO.3 or NO.5 or a protein consisting of an amino acid sequence formed as a result of the deletion, substitution or addition of one or more amino acids in said protein. An inventive protein to be transferred to the cell membrane is preferably a transporter protein whose function can not be identified because of the inability to be transferred to a cell membrane in an exogenous gene expression system.

EXAMPLES

The invention is further described in detail by the following EXAMPLES which are not intended to restrict the invention.

Unless otherwise specified, each procedure of the following EXAMPLES was conducted in accordance with the methods described in Molecular Cloning (Sambrook, J., Fritsh, E. F. and Manitis, T., Cold Spring Harbor Press, 1989) or a manufacture's instruction when using a commercial reagent or kit.

Example 1

(1) Identification of Mouse cDNA of Sodium-independent Transporter Transporting Small-sized Neutral Amino Acid A cDNA clone, corresponding to a mouse-derived base sequence GenBank™/EBI/DDBJ accession No. AI875555 analogous to the rat LAT1 obtained by searching the EST (expressed sequence tag) database employing the base sequence of the translation region of the rat LAT1 [Kanai et al., J. Biol. Chem. 273: 23629-23632, 1998], was purchased from IMAGE (Integrated and Molecular Analysis of Genomes and their Expression) (IMAGE clone I.D.: 1972372), and subjected to a dye terminator cycle sequencing method (Applied Biosystems) using synthetic primers for a base sequencing to determine the full-length base sequence of the cDNA. The base sequence of the cDNA was analyzed by an ordinary method to determine the translation region of the cDNA and the amino acid sequence of a protein encoded thereby.

This amino acid sequence is represented by SEQ ID NO.1 in the following sequence listing and the base sequence is represented by SEQ ID NO.2.

The Asc-2 comprised the 34% homology of amino acid sequence with a rat transporter LAT1 corresponding to a neutral amino acid transport system L and 33% with the LAT2. The Asc-2 also comprised the 34% homology with a rat transporter y$^+$LAT1 corresponding to a neutral and basic amino acid transport system y$^+$L and 32% with a human transporter y$^+$LAT2. Further, the Asc-2 comprised the 34% homology of amino acid sequence with a mouse transporter xCT corresponding to a cystine and acidic amino acid transport system x$^-$C and 35% with a rat transporter BAT1 corresponding to a cystine and neutral and basic amino acid transport system b$^{0,+}$. Furthermore, the Asc-2 comprised a 28 to 29% homology with mouse and human transporter CAT 1 to 4 corresponding to a basic amino acid transport system y$^+$.

Figure 1:
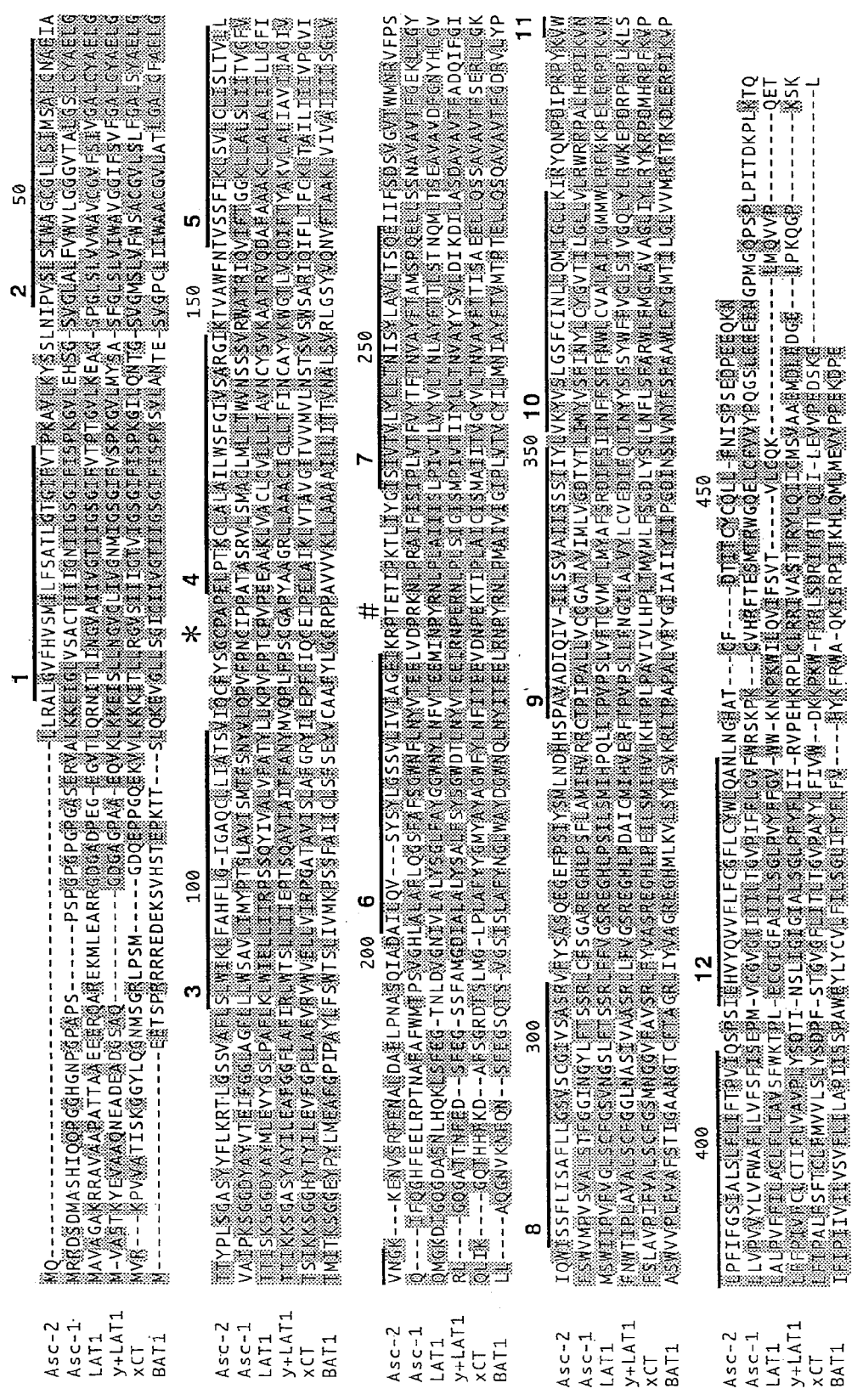

The amino acid sequences of mouse Asc-2 and mouse Asc-1, ratLAT1, rat y$^+$LAT1, human y$^+$LAT2, mouse xCT and rat BAT1 were compared in FIG. 1.

Based on a SOSUI algorithm [Hirokawa, T. et al., Bioinformatics, Vol. 14, page 378 (1998)], the amino acid sequence of the Asc-2 was analyzed and 12 membrane-spanning domains were assumed as shown in FIG. 1. The 3rd hydrophilic loop contained a cysteine residue conserved among the LAT1, LAT2, Asc-2, y$^+$LAT1, y$^+$LAT2, xCT and BAT1. This cysteine residue was assumed to bind the Asc-2 to an unknown cofactor via its disulfide bond. The 6th hydrophilic loop contained a site which was assumed to a cAMP-dependent phosphorylation site.

(2) Asc-2 Protein Analysis by In Vitro Translation

By means of an in vitro translation method [Hediger et al., Biochim. Biophys. Acta, Vol. 1064, page 360, 1991], Asc-2 and 4F2hc proteins were synthesized from the Asc-2 cRNA and a mouse 4F2hc cRNA, and subjected to an electrophoresis.

The results are shown as a photograph substituted for the drawing in FIG. 2. As evident from this, a 55 kDa band was observed, which proved that no sugar was added in the presence of a canine pancreas microsome fraction containing a series of sugar addition enzymes, indicating a protein having no sugar addition site (see FIG. 2). On the contrary, the in vitro translation of the 4F2hc cRNA conducted as a control of the sugar addition reaction exhibited a 65 kDa band, and a 80 kDa band was observed in the presence of canine pancreas microsome fraction. This band was reverted to a 65 kDa band by the saccharide chain cleavage endoglycosidase H.

(3) Expression of Asc-2 Gene in Various Tissues of Mouse (Analysis by Northern Blotting)

A cDNA fragment corresponding to the 135th to 735th base pairs of the Asc-2 gene was amplified by a PCR, labeled with $^{32}$P-dCTP, and used as a probe to conduct the northern blotting for the RNA extracted from various tissues of a mouse as described below. 3 μg of a poly(A)$^+$RNA was subjected to an electrophoresis on a 1% agarose/formaldehyde gel and transferred onto a nitrocellulose filter. This filter was subjected to a hybridization overnight in a hybridization solution containing a cDNA fragment of the Asc-2 labeled with $^{32}$P-dCTP at 42° C. The filter was washed with 0.1×SSC containing 0.1% SDS at 65° C.

Figure 3:
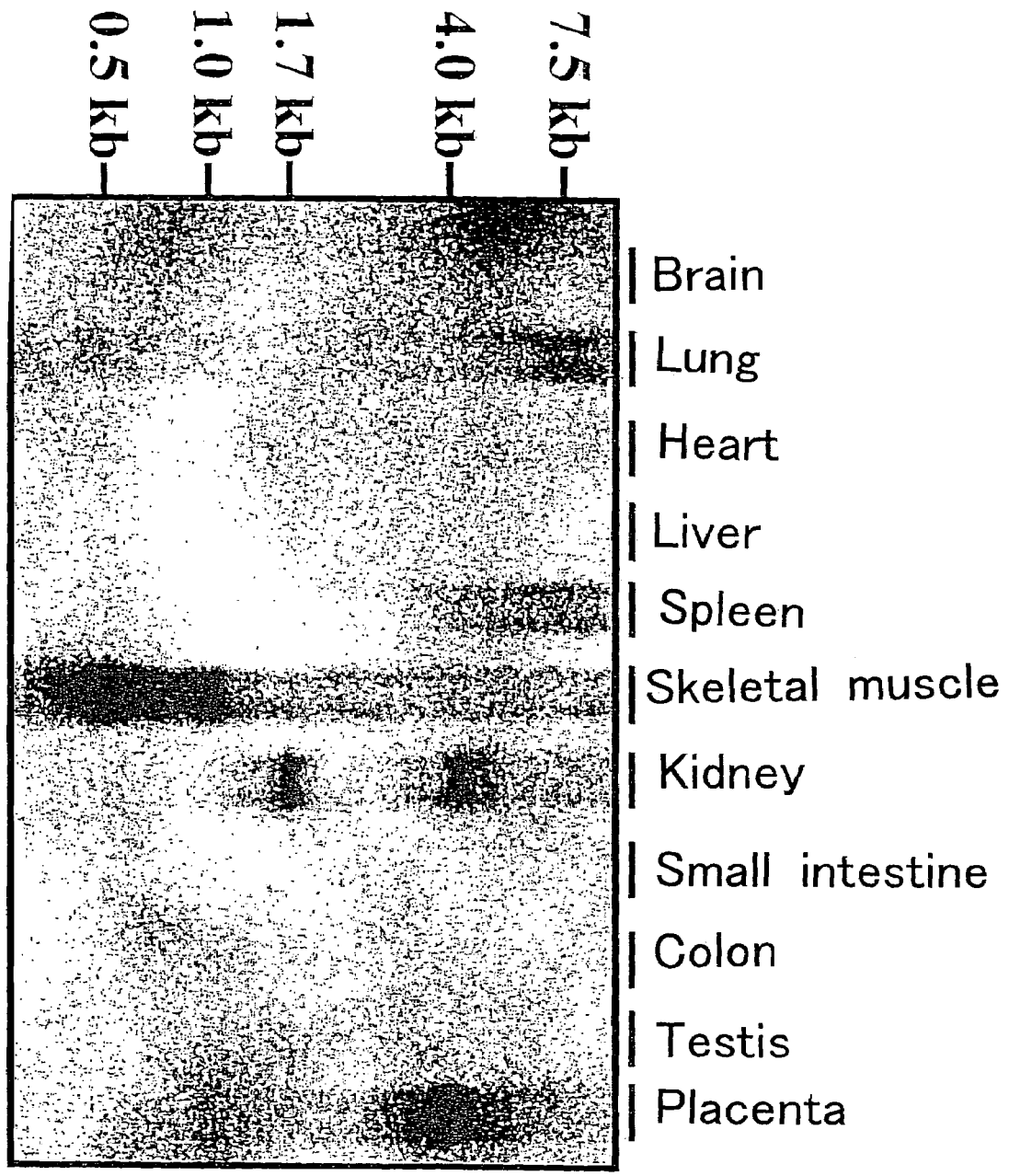
FIG. 3 is a photograph substituted for the drawing showing the results of the northern blotting analysis of the expression of the Asc-2 gene mRNA in various organs of a mouse. From the left of the figure, the brain, lung, heart, liver, spleen, skeletal muscle, kidney, small intestine, colon, testis and placenta are indicated in this order. The numbers on the left indicate the positions of the molecular weight markers.

The results of the northern blotting are shown as a photograph substituted for the drawing in FIG. 3. As a result, the kidney exhibited a band near 1.7 kb. The kidney and the placenta exhibited a band near 4.0 kb. A less intense band near 7.5 kb was exhibited by the lung and the spleen. The skeletal muscle exhibited short bands near 0.5 kb and 1.0 kb.

Also for the purpose of examining whether the Asc-2 is expressed in an erythrocyte or not, a method by Hara et al (Hara, H. and Ogawa. M.: Am. J. Hematol. 1: 453-458, 1976) was employed to develop a hemolytic anemia in a male ICR mouse by administering 1-acetyl-2-phenylhydrazine (60 mg/kg body weight) on the 0th, 1st and 3rd days whereby inducing a splenic hematopoiesis, and then the spleen was taken out on the 6th day. 3 μg of the poly(A)$^+$ RNA extracted from this spleen was subjected together with the poly(A)$^+$RNA (3 μg) of the spleen derived from a non-treated male ICR mouse to an electrophoresis on a 1% agarose/formaldehyde gel and transferred onto a nitrocellulose filter. This filter was subjected to a hybridization overnight in a hybridization solution containing a cDNA fragment of the Asc-2 labeled with $^{32}$P-dCTP at 42° C. The filter was washed with 0.1×SSC containing 0.1% SDS at 65° C. At the same time, a northern hybridization using as a probe a cDNA fragment of a mouse Asc-1 labeled with $^{32}$P-dCTP was conducted.

Figure 4:
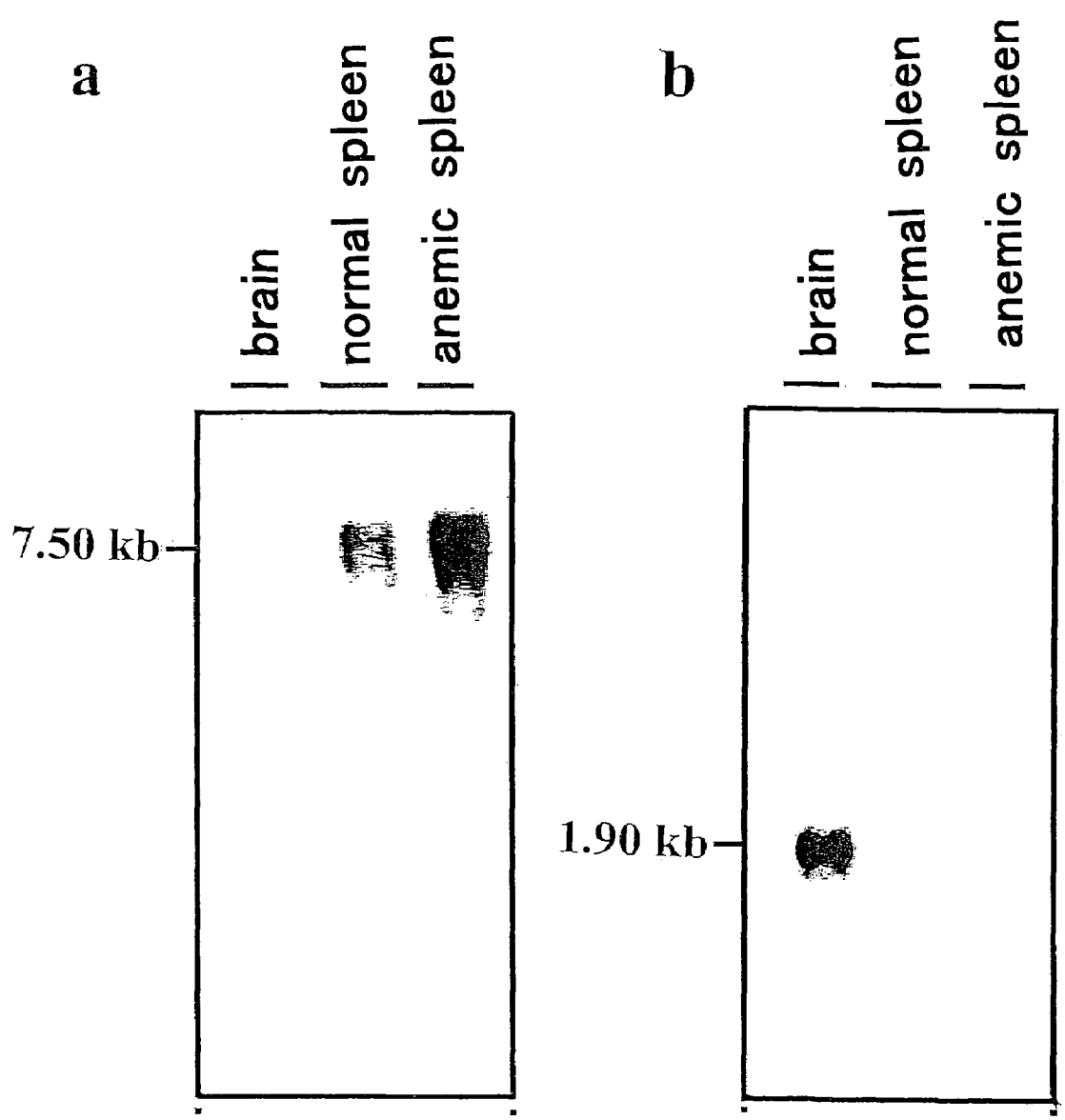
FIG. 4 is a photograph substituted for the drawing showing the results of the northern blotting analysis of the expression of the Asc-2 gene mRNA (FIG. 4a) and the expression of the Asc-1 gene mRNA (FIG. 4b) in a mouse brain, a normal mouse spleen and a hemolytic anemia mouse spleen. The expression of the Asc-2 gene mRNA is higher in the hemolytic anemia mouse spleen (anemic spleen) than in the normal mouse spleen, while it was not observed in the brain (FIG. 4a). On the contrary, the expression of the Asc-1 gene mRNA was observed only in the brain, and was not observed in either of the normal mouse spleen or the hemolytic anemia mouse spleen (FIG. 4b).

The results of this northern blotting are shown as a photograph substituted for the drawing in FIG. 4. As a result, the both of the non-treated mouse spleen and the 1-acetyl-2-phenylhydrazine-treated mouse spleen exhibited a band near 7.5 kb. The expression in the 1-acetyl-2-phenylhydrazine-treated mouse was higher by 3.2±0.6 (mean±standard error, n=3) than that in the non-treated mouse. Accordingly, it was suggested that the Asc-2 was expressed in the erythrocyte. On the contrary, the Asc-1 was expressed only in the brain, and no expression in the spleen was noted either in the non-treated mouse or in the 1-acetyl-2-phenylhydrazine-treated mouse.

(4) Expression of Asc-2 Protein in Mouse Erythrocyte and Mouse Kidney

A specific antibody directed to a synthetic oligopeptide corresponding to the 455-465 of a mouse Asc-2 [SPSED-PEEQKNC] (cysteine residue at the C-terminal was introduced for the conjugation with KLH (keyhole limpet hemocyanine)) (SEQ ID NO: 16) was prepared in accordance with a method by Altman et al (Altman et al., Proc. Natl. Acad. Sci. USA, Vol. 81, page 2176-2180, 1984).

Membrane fractions of the erythrocyte and the kidney of a mouse were prepared in accordance with a method by Thorens et al [Thorens et al., Cell Vol. 55, page 281 to 290, 1988]. A protein sample was treated for 5 minutes at 100° C. in the presence (reducing condition) or absence (non-reducing condition) of 5% 2-mercaptoethanol, subjected to an electrophoresis on an SDS-polyacrylamide gel, blotted onto a Hybond-P PVDV transfer membrane, and treated with an anti-Asc-2 affinity purified antibody (1:5000).

Figure 5:
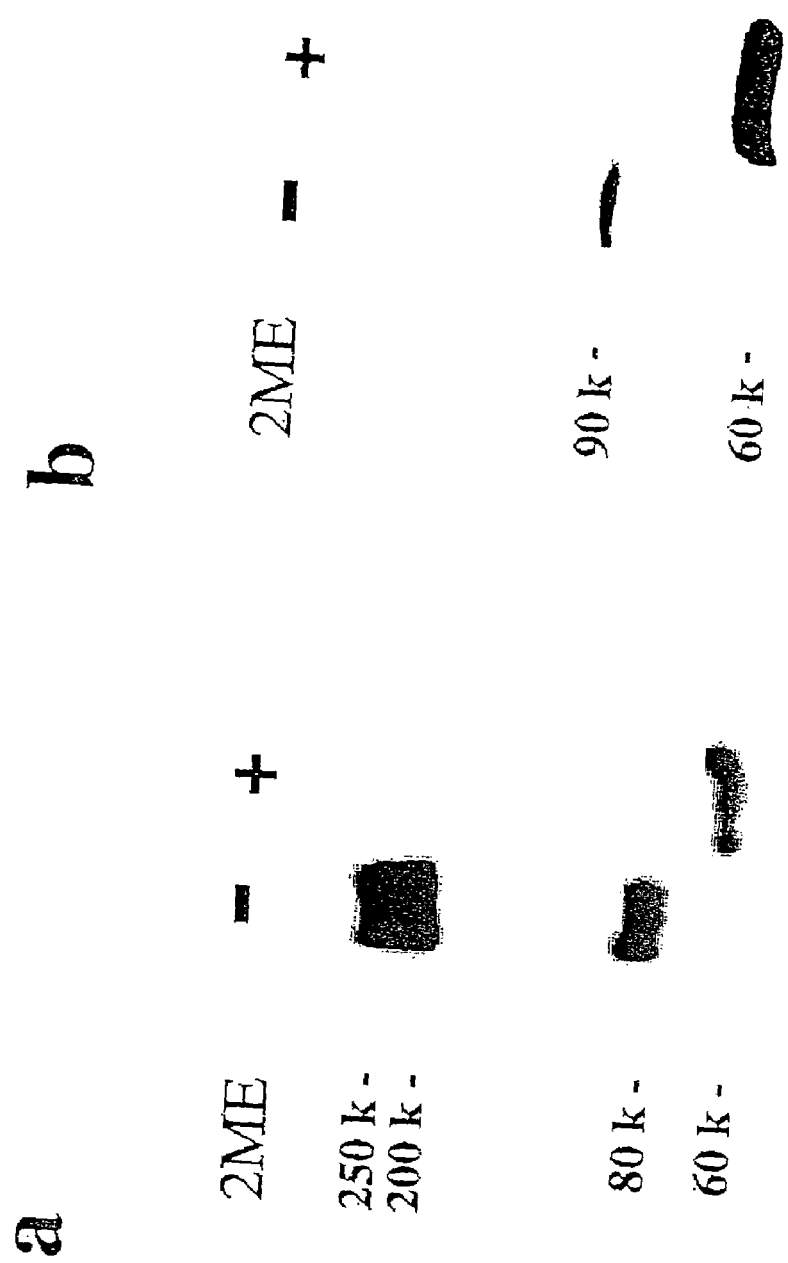
FIG. 5 is a photograph substituted for the drawing showing the results of the western blotting analysis using an anti-Asc-2 antibody in a mouse erythrocyte membrane specimen (FIG. 5a) and a mouse kidney membrane specimen (FIG. 5b). The both were tested under a non-reducing condition (−) and a reducing condition (+).

The results are shown as a photograph substituted for the drawing in FIG. 5. The mouse erythrocyte exhibited, in response to the anti-Asc-2 antibody, the bands near 80 kDa, 200 kDa and 250 kDa under the non-reducing condition as shown in FIG. 5. The mouse kidney exhibited a band near 90 kDa. Under the reducing condition, both of the erythrocyte and the kidney exhibited a band near 60 kDa. Based on these results, the Asc-2 was suggested to be bound to some protein via a disulfide bond. In addition, it is also suggested that there is a difference between the erythrocyte and the kidney in the protein bound to the Asc-2.

Example 2

Figure 6:
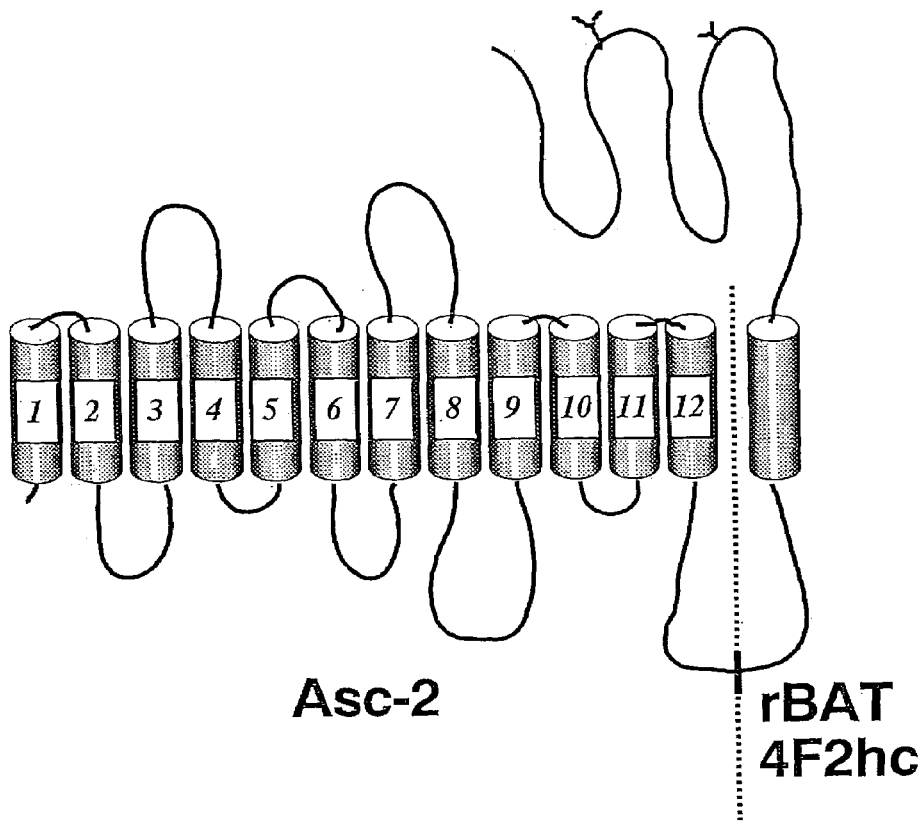
FIG. 6 shows a schematic view of the structure of the fusion protein formed by connecting the Asc-2 to the rBAT or the 4F2hc. The cylindrical part represents a membrane-spanning region. The lower column of FIG. 6 indicates the amino acid sequences and the respective gene base sequences of the connection parts of the Asc-2-rBAT fusion protein (SEQ ID NOS 12-13) and the Asc-2-4F2hc fusion protein (SEQ ID NOS 14-15). Asc-2, SEQ ID NO: 1 (amino acid) SEQ ID NO: 2 (base): rBAT SEQ ID NO: 5 (amino acid) SEQ ID NO: 6 (base): 4F2hc SEQ ID NO:3 (amino acid) SEQ ID NO: 4 (base).

Preparation of Fusion Protein of Sodium-independent Transporter Asc-2 Transporting Small-sized Neutral Amino Acid with 4F2hc or rBAT and Analysis of its Function (1) Preparation of Fusion Protein of Sodium-independent Transporter Asc-2 Transporting Small-sized Neutral Amino Acid with 4F2hc or rBAT A fusion protein of the Asc-2 with the rBAT (Asc-2-rBAT) was prepared by using synthetic oligo DNA primers 5'-GCGCGAATTCAAGCTTGAACACCCT-GTTTGACAGGG-3' (SEQ ID NO: 17) (a sequence corresponding to the 17th to 36th base pairs of a cDNA of the Asc-2 combined with a sequence corresponding to the HindIII and EcoRI cleavage sites and GCGC at the 5'-terminal) and 5'-GCGCGAATTCACTAGTATTTTTCTGT-TCTTCTGGAT-3' (SEQ ID NO: 18) (a sequence corresponding to the 1491st to 1510th base pairs of a cDNA of the Asc-2 combined with a sequence corresponding to the SpeI and EcoRI cleavage sites and GCGC at the 5' terminal) together with a cDNA of the Asc-2 as a template to conduct a PCR. The resultant PCR product was cleaved with HindIII and EcoRI and ligated to the HindIII and EcoRI sites of a mammalian cell expression vector pcDNA3.1(+) (Invitrogen). On the other hand, synthetic oligo DNA primer 5'-GCGCATCGATAGCCAGGACACCGAAGTGGA-3' (SEQ ID NO: 19) (a sequence corresponding to the 20 base pairs immediately after the translation initiation codon ATG of the mouse rBAT represented by SEQ ID NO.6 combined with a sequence corresponding to the EcoRI cleavage site and GCGC at the 5' terminal) and 5'-GCGCGCGGCCGC-CATATTTAAATGCTTTAGTA-3' (SEQ ID NO: 20) (a sequence corresponding to the 2240th to 2259th base pairs of the mouse rBAT represented by SEQ ID NO.6 combined with a sequence corresponding to the NotI cleavage site and GCGC at the 5' terminal) were employed together with a cDNA of the rBAT as a template to conduct a PCR. The resultant PCR product was cleaved with EcoRI and NotI and ligated to the EcoRI and NotI sites of a mammalian cell expression vector pcDNA3.1 (+) into which the PCR product of the Asc-2 had been integrated as described above to obtain a cDNA encoding the fusion protein of the Asc-2 with the 4F2hc (see FIG. 6).

Figure 7:
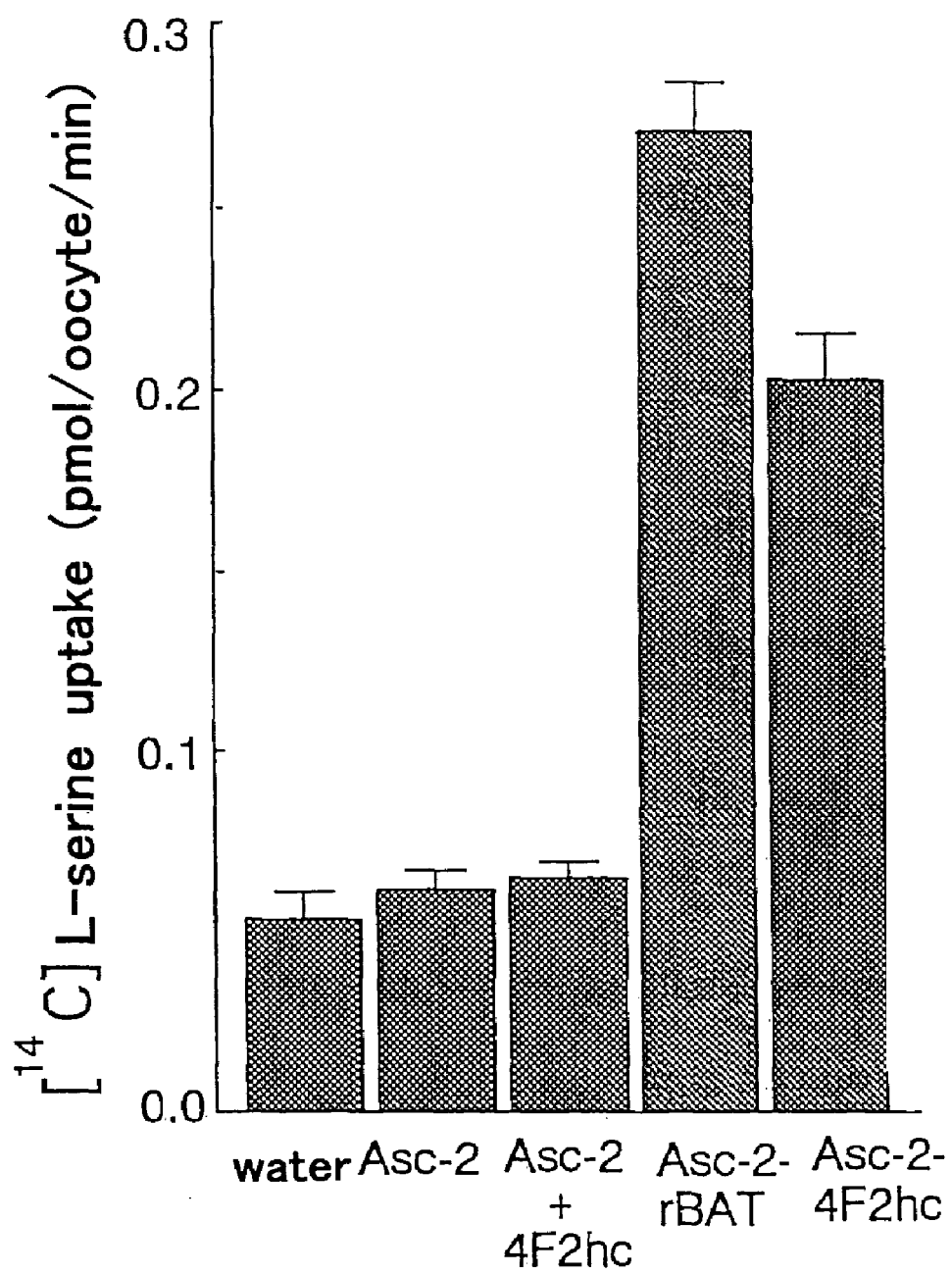
FIG. 7 shows the results of the experiment investigating the uptake of serine by an oocyte into which the Asc-2 gene cRNA, Asc-2 gene cRNA plus mouse 4F2hc gene cRNA, Asc-2-rBAT fusion protein gene cRNA and the Asc-2-4F2hc fusion protein gene cRNA were injected. The "water" indicated on the left end means a control into which water was introduced, and the ordinate of the graph indicates the serine uptake (pmol/oocyte cell/min).

(2) The results of the $^{14}$C-serine uptake test in oocytes are shown in FIG. 7. The levels of the $^{14}$C-serine uptake in the oocyte where only the Asc-2 was expressed and the oocyte where the Asc-2 and the 4F2hc were co-expressed were similar to that in the control oocyte into which water was injected, while a higher serine uptake was noted in the oocyte where the Asc-2-rBAT or the Asc-2-4F2hc was expressed.

It was examined that the rBAT or the 4F2hc does not serve as a direct cofactor for the Asc-2 using a COS-7 cell. A plasmid DNA (each 1 μg) containing the cDNA of the Asc-2, cDNA of the rBAT or cDNA of the 4F2hc was introduced into the COS-7 cell using a Lipofectamine 2000 reagent (life Technologies) in accordance with a method by Mizoguchi et al (Kidney Int. 59: 1821-1833, 2001). After the introduction, the cell was incubated in a 24-well plate for 2 days and then the uptake of $^{14}$C-serine (10 μM) was measured. In accordance with the method of Mizoguchi et al. [Mizoguchi et al.: Kidney Int. 59: 1821-1833, 2001], the measurement of the uptake was initiated by removing the culture medium and adding a Dulbecco's PBS (Gibco) containing $^{14}$C-serine, which was subsequently removed and the measurement was terminated by washing the plate with an ice-cooled Dulbecco's PBS. After the washing it was dissolved in 0.1N NaOH, and the radioactivity was measured by a liquid scintillation counting.

Figure 8:
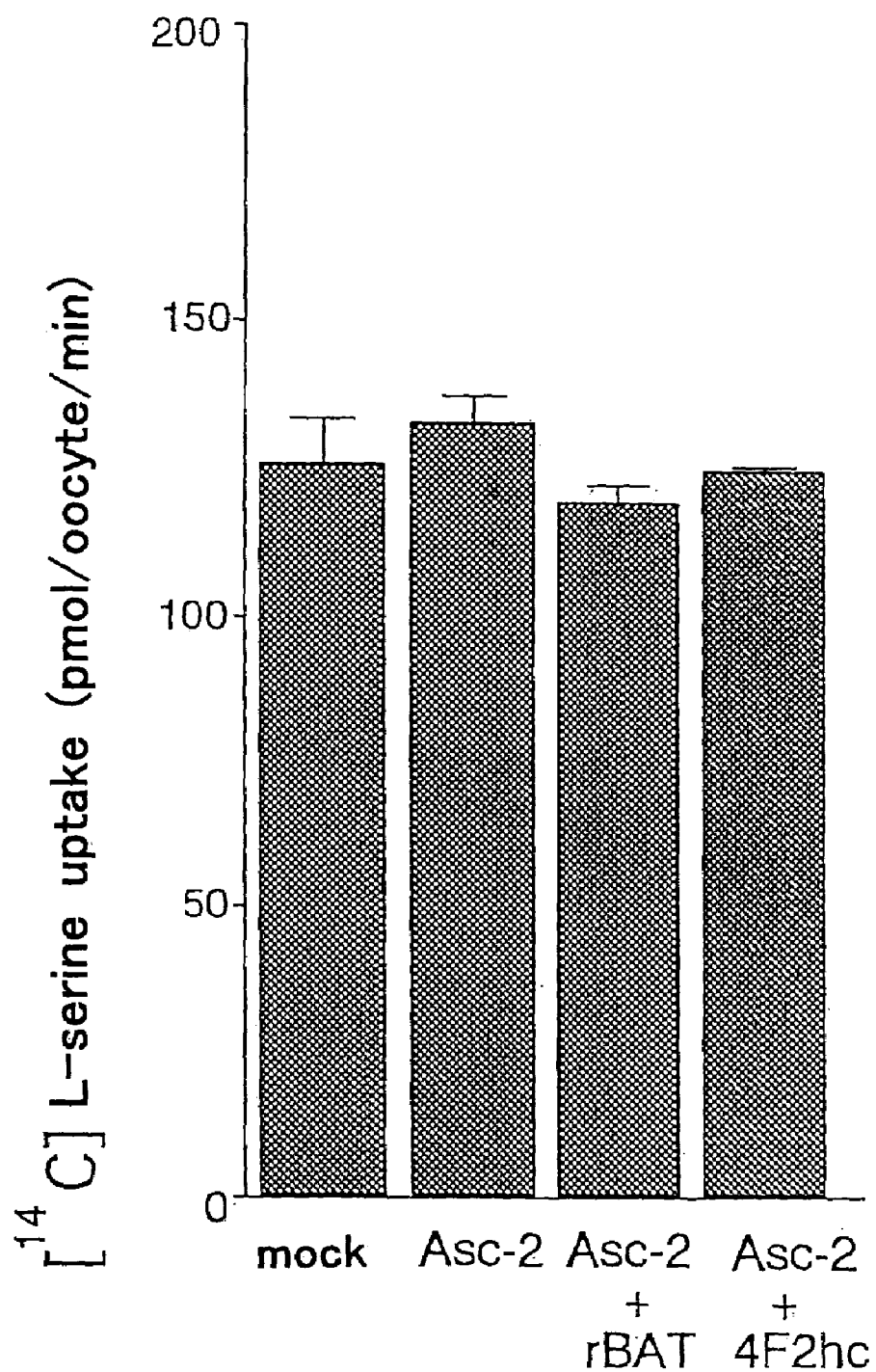
FIG. 8 shows the results of the experiment investigating the uptake of serine by a COS-7 cell into which the Asc-2 gene, Asc-2 gene plus mouse rBAT gene and Asc-2 gene plus mouse 4F2hc gene were introduced. The left end shows the results of a control test (mock), and the ordinate of the graph indicates the serine uptake (pmol/cell/min).

The results are shown in FIG. 8. The levels of the serine uptake in the oocyte where only the Asc-2 was expressed and the oocyte where the Asc-2 and the rBAT were co-expressed and also in the oocyte where the Asc-2 and the 4F2hc were co-expressed were similar to that in the control oocyte into which water was injected. It proved that the rBAT or the 4F2hc does not serve as a direct cofactor for the Asc-2.

(3) Identification of Expression of Fusion Protein of Sodium-independent Transporter Asc-2 Transporting Small-sized Neutral Amino Acid with 4F2hc (Asc-2-4F2hc) in Oocyte Cell Membrane by Fluoroimmunoassay Whether the fact that no function was observed when allowing Asc-2 to express in oocyte but the fusion protein of the Asc-2 with the 4F2hc (Asc-2-4F2hc) exhibited a functional activity is attributable to the inability of the Asc-2 to be transported to the cell membrane and the ability of the Asc-2-4F2hc to be transported to the cell membrane or not was verified by a fluoroimmunoassay.

25 ng of the Asc-2 gene cRNA or 25 ng of the cRNA of the gene of the fusion protein of the Asc-2 with the 4F2hc (Asc-2-4F2hc) was injected into an oocyte and allowed to be expressed, and after incubating for 3 days the oocyte was fixed in a 4% paraformaldehyde-phsophate buffer solution, and subjected to an ordinary method to obtain a paraffin section (3 μm). After removing the paraffin, the section was blocked with 5% goat serum in a 0.05M tris-buffered physiological saline containing 0.1% Tween 20, and then treated with an affinity-purified anti-Asc-2 antibody or an affinity-purified anti-4F2hc antibody [Fukasawa et al., J. Biol. Chem. 275: 9690-9698, 2000]. Thereafter, the section was treated with a Cy3-labeled goat anti-rabbit IgG (Jacson ImmunoResearch Laboratories), washed with a 0.05M tris-buffered physiological saline containing 0.1% Tween 20, and then observed with an Olympus Fluoview (FV 500) confocal laser microscope (Olympus). The excitation was effected with a Green Hanere laser at 543 nm, and the fluorescence from the Cy3 was detected using a BA560IF filter.

Figure 9:
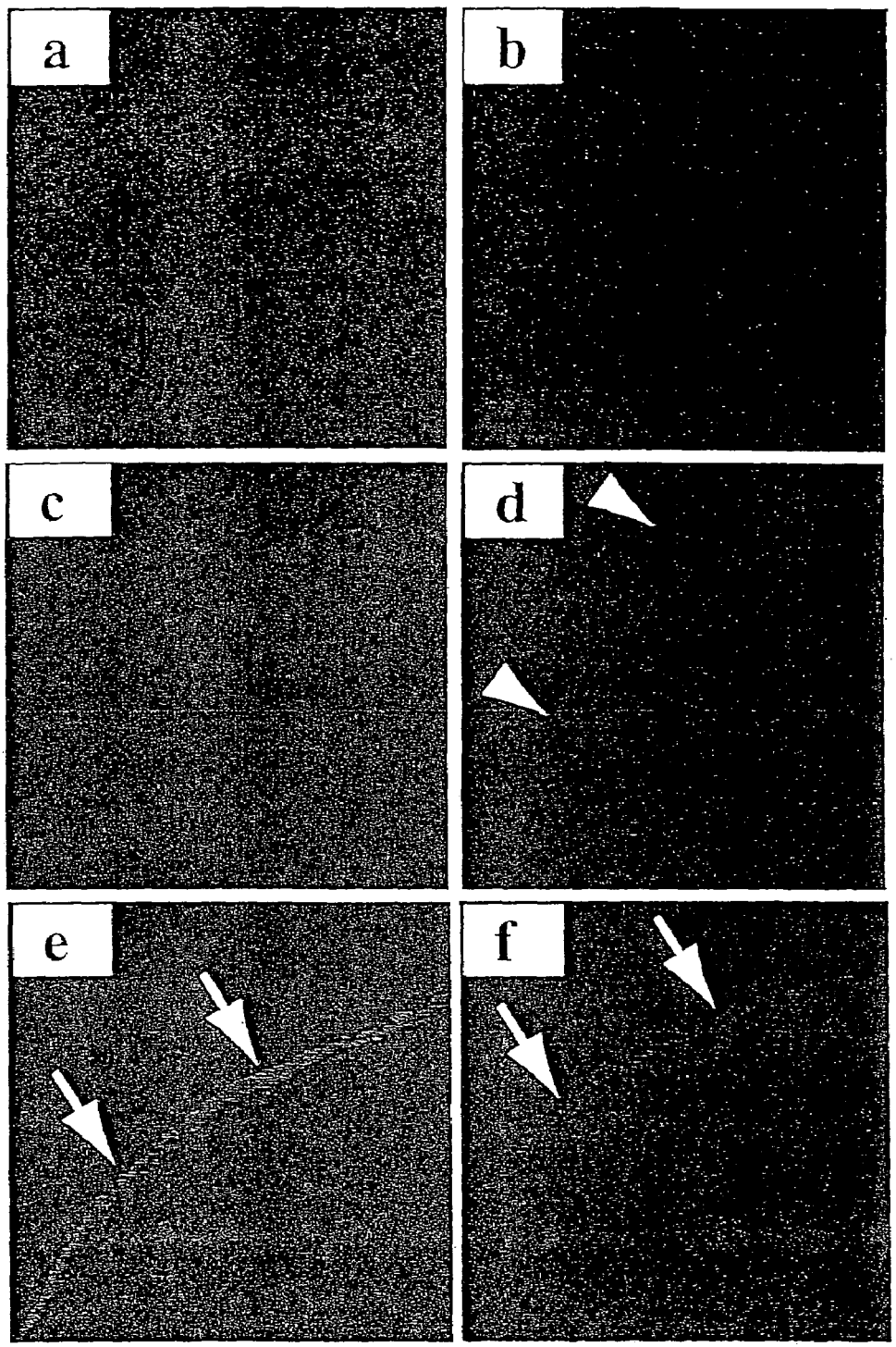
FIG. 9 is a photograph substituted for the drawing showing the results of the fluoroimmunoassay of the expression of the fusion protein of the Asc-2 with the 4F2hc (Asc-2-4F2hc) in an oocyte cell membrane. A control oocyte into which water was injected (FIGS. 9a and b), an oocyte into which the Asc-2 gene cRNA was injected and expressed (FIGS. 9c and d) and an oocyte into which the cRNA of the gene of the fusion protein of the Asc-2 with the 4F2hc (Asc-2-4F2hc) was injected and expressed (FIGS. 9e and f) were subjected to the test using an anti-4F2hc antibody (a, c and e) or an anti-Asc-2 antibody (b, d and f). The part exhibiting the fluorescence is designated by an arrow. The detected Asc-2 protein was not present on the cell membrane and was remaining within the cytoplasm (FIG. 9d), while in the oocyte in which the fusion protein of the Asc-2 with the 4F2hc (Asc-2-4F2hc) was expressed both of the anti-4F2hc antibody (FIG. 9e) and the anti-Asc-2 antibody (FIG. 9f) detected the Asc-2-4F2hc fusion protein expressed on the cell membrane.

The results are shown as a photograph substituted for the drawing in FIG. 9. The Asc-2 protein detected by the anti-Asc-2 antibody in the oocyte where the Asc-2 was expressed was not present on the cell membrane and was remaining within the cytoplasm (FIG. 9d), while in the oocyte where the fusion protein of the Asc-2 with the 4F2hc (Asc-2-4F2hc) was expressed the both of the anti-4F2hc antibody (FIG. 9e) and the anti-Asc-2 antibody (FIG. 9f) allowed the Asc-2-4F2hc fusion protein expressed on the cell membrane to be detected. The control oocyte into which water was injected exhibited no specific color development in response to the anti-4F2hc antibody (FIG. 9a) or the anti-Asc-2 antibody (FIG. 9b). Accordingly, it was proven that the fact that no function was observed when allowing the oocyte to express the Asc-2 while the fusion protein of the Asc-2 with the 4F2hc (Asc-2-4F2hc) exhibited a functional activity is attributable to the inability of the Asc-2 to be transported to the cell membrane and the ability of the fusion protein with the 4F2hc (Asc-2-4F2hc) to be transported to the cell membrane.

(4) Salt Dependency of Asc-2 Transport Activity

In a serine uptake test in an oocyte into which a cRNA of the gene of the fusion protein of the Asc-2 with the 4F2hc or the rBAT (Asc-2-4F2hc or Asc-2-rBAT) was injected, the effect of a salt added to a culture medium was investigated.

The serine uptake test was conducted using the oocyte into which a cRNA of the gene of the fusion protein of the Asc-2 with the 4F2hc or the rBAT (Asc-2-4F2hc or Asc-2-rBAT) was injected in accordance with the method in Section (2) in Example 2 described above. Nevertheless, the test was conducted using as an uptake solution for investigating the effect of sodium a standard uptake solution (100 mM sodium chloride instead of 100 mM choline chloride) instead of the sodium-free uptake solution (Na+-free uptake solution). The test was conducted also using as an uptake solution for investigating the effect of chloride ion a gluconic acid uptake solution (100 mM sodium gluconate instead of 100 mM sodium chloride) instead of a standard uptake solution.

Figure 10:
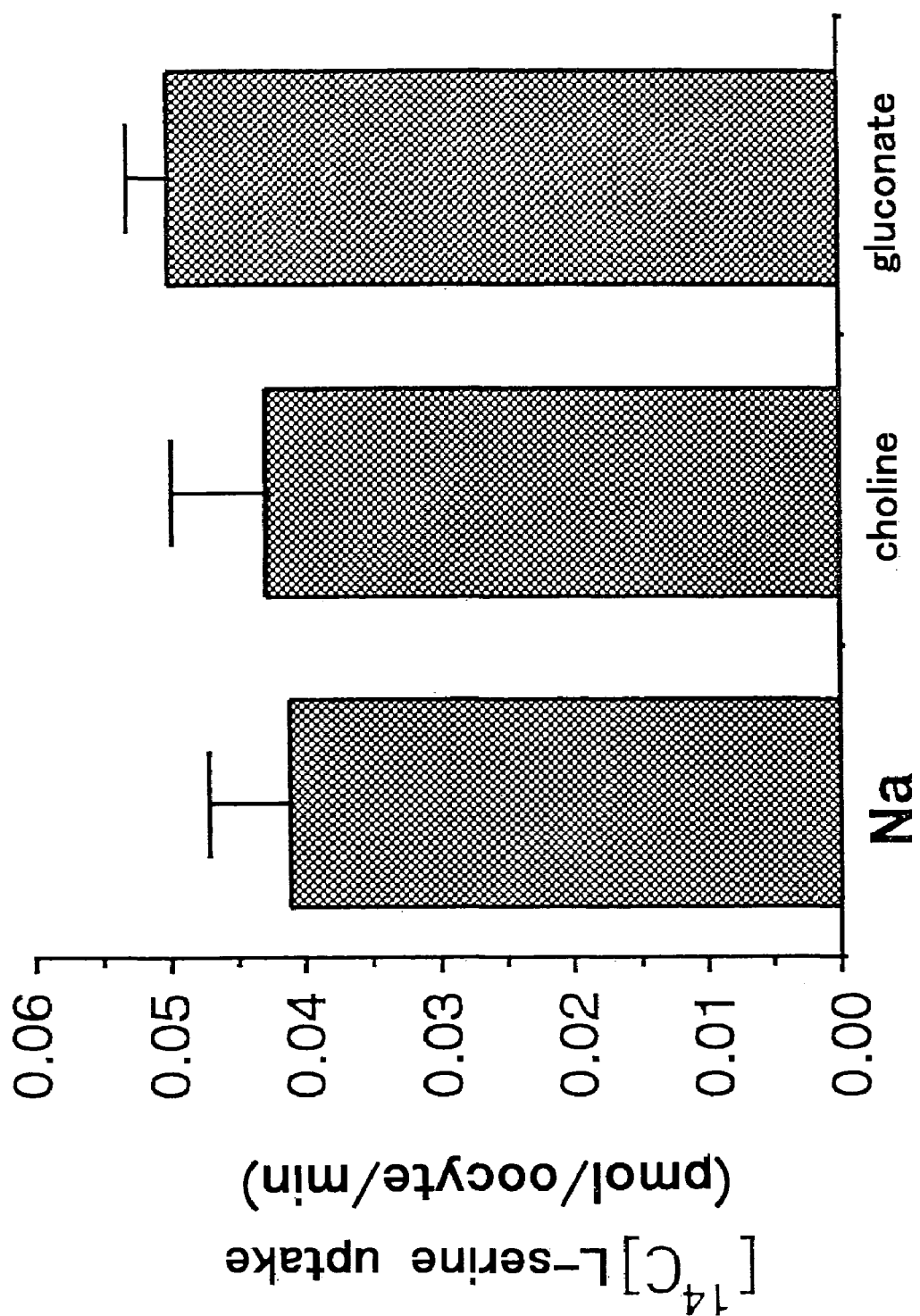
FIG. 10 shows the results of the experiment investigating the effects of salts added in the experiment of the serine uptake by the oocyte into which the cRNA of the gene of the fusion protein of the Asc-2 and the rBAT (Asc-2-rBAT) was injected. From the left, sodium chloride, choline chloride and sodium gluconate are indicated in this order. The ordinate of the graph indicates the serine uptake (pmol/oocyte/min).

The results are shown in FIG. 10. Even when exchanging the extracellular choline with sodium, or when exchanging the extracellular chloride ion with the gluconate ion, the serine uptake was not influenced at all. Accordingly, it was suggested that the Asc-2 is a transporter which acts independently of the sodium ion or the chloride ion.

(5) Michaelis-Menten Pharmacodynamic Test of Asc-2

A Michaelis-Menten pharmacodynamic test of a sodium-independent transporter Asc-2 transporting small-sized neutral amino acid was conducted. By investigating the change in the ratio of serine uptake by the difference in the substrate serine concentration, the Michaelis-Menten pharmacodynamic test of the Asc-2 was conducted.

Figure 11:
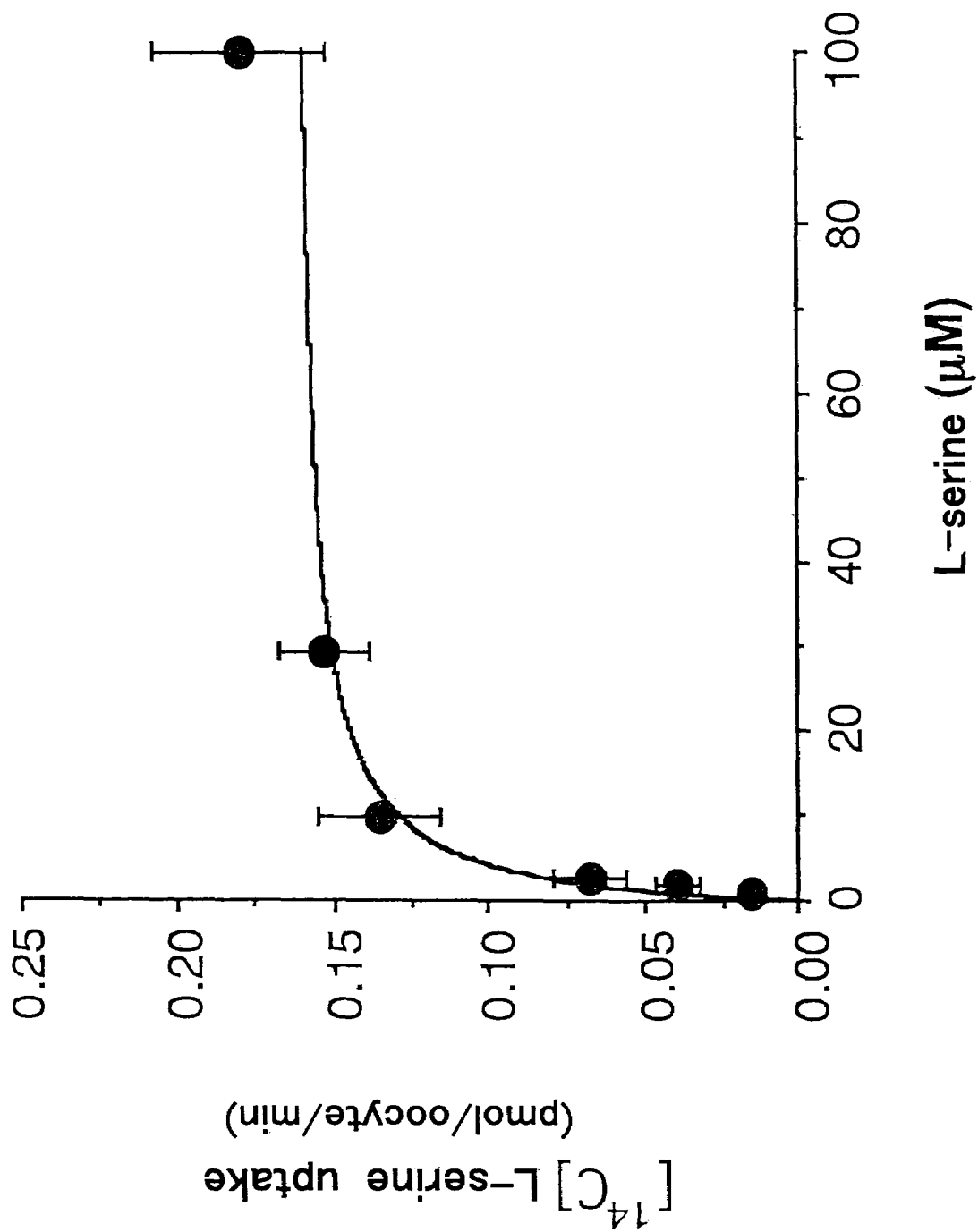
FIG. 11 shows the results of the experiment investigating the effects of the substrate serine concentration in the experiment of the serine uptake by the oocyte into which the cRNA of the gene of the fusion protein of the Asc-2 and the rBAT (Asc-2-rBAT) was injected. The abscissa of the graph indicates the serine concentration (μM) while the ordinate indicates the serine uptake (pmol/oocyte/min).

The serine uptake test was conducted using the oocyte into which a cRNA of the gene of the fusion protein of the Asc-2 with the 4F2hc or the rBAT (Asc-2-4F2hc or Asc-2-rBAT) was injected in accordance with the method in Section (2) in Example 2 described above. The results are shown in FIG. 11. The Km value of the serine transport of the Asc-2-rBAT was 2.88±0.37 μM (mean±standard error, n=3). The Km value of the serine transport of the Asc-2-4F2hc was 2.10 μM.

The Michaelis-Menten pharmacodynamic tests were conducted also for the amino acids, other than serine, which also serve as the substrates for the Asc-2, and the Km and Vmax values were calculated and are shown in the following Table 1.

TABLE 1

Km and Vmax values of substrate amino acids

| Amino acid | Km[a] μM | Vmax[b] |
|---|---|---|
| L-Serine | 2.88 ± 0.37 | (1.00) |
| L-Alanine | 2.35 ± 0.30 | 0.83 ± 0.08 |
| L-Threonine | 2.72 ± 0.44 | 0.53 ± 0.06 |
| L-Cysteine | 3.13 ± 0.57 | 0.19 ± 0.03 |
| Glycine | 2.15 ± 0.35 | 1.18 ± 0.05 |
| L-Valine | 34.8 ± 10.6 | 0.79 ± 0.22 |
| L-Leucine | 39.6 ± 4.3 | 1.17 ± 0.11 |

[a],[b]The Vmax value of each amino acid is shown by the ratio to the Vmax of serine. Each of the Km and Vmax values is represented by mean ± standard error (n = 3).

Each Vmax value in Table 1 is a ratio based on the Vmax of alanine being regarded as 1.00. Each values is represented by mean±standard error (n=3).

(6) Asc-2-mediated Amino Acid Release Test

In an oocyte into which a cRNA of the gene of the fusion protein of the Asc-2 and with the rBAT (Asc-2-rBAT) had been injected together, the release of $^{14}$C-serine loaded as described above via the Asc-2 was investigated.

Into the oocyte into which a cRNA of the gene of the fusion protein of the Asc-2 and the rBAT (Asc-2-rBAT) had been injected, 100 nl of 600 μM $^{14}$C-serine (~10 nCi) was injected, and the cell was washed with an ice-cooled sodium-free uptake solution (Na+-free uptake solution) which does not contain serine, and then transferred into a sodium-free uptake solution (Na+-free uptake solution) in the presence or absence of serine (100 μM) at room temperature (18 to 22° C.), and then examined for the level of $^{14}$C-serine released from the cell.

Figure 12:
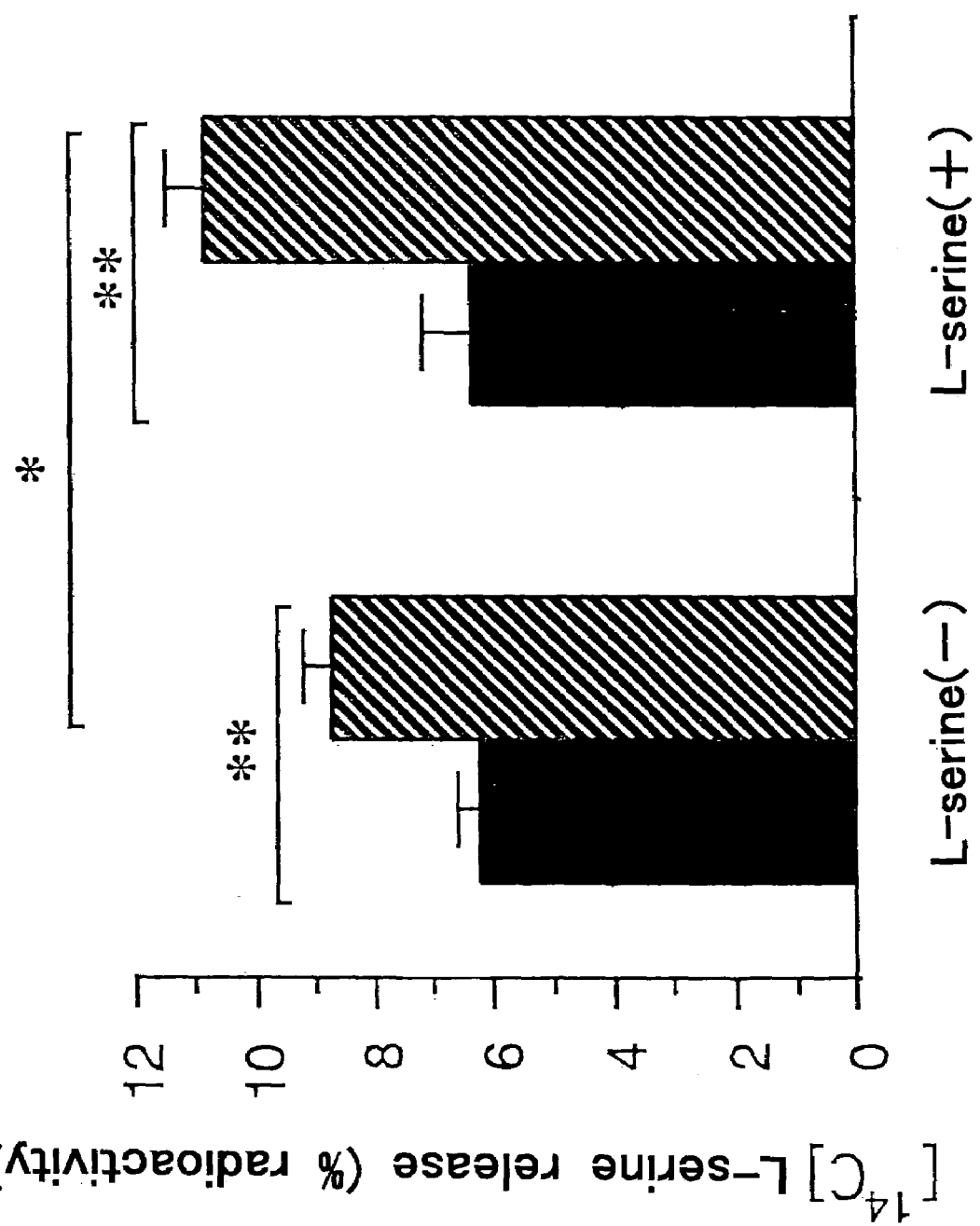
FIG. 12 shows the results of the investigation of the release of $^{14}$C-serine from an oocyte into which the cRNA of the gene of the fusion protein of the Asc-2 and the rBAT (Asc-2-rBAT) was injected in the presence (+) or absence (−) of the extracellular non-labeled serine (100 μM). The ordinate indicates a released radioactivity as % based on the radioactivity injected into the oocyte. The solid column indicates a control oocyte into which water was injected instead of the cRNA, and the hatched column indicates the oocyte into which the Asc-2-rBAT gene cRNA was injected. The designation "*" or "**" indicates a significant difference.

The results are shown in FIG. 12. The Asc-2-rBAT exhibited a significant release of $^{14}$C-serine even in the absence of the extracellular serine, and the release was increased in the presence of the extracellular serine (FIG. 12). Accordingly, the Asc-2 is revealed to be a mixed transporter of the exchange transport and a facilitated diffusion type transport.

similarly to the Asc-2-rBAT, in an oocyte into which a cRNA of the gene of the fusion protein of the Asc-2 with the 4F2hc (Asc-2-4F2hc) had been injected together, the release of $^{14}$C-serine loaded as described above via the Asc-2 was also investigated.

As a result, the Asc-2-4F2hc exhibited, similarly to the Asc-2-rBAT, a significant release of $^{14}$C-serine even in the absence of the extracellular serine, and the release was increased in the presence of the extracellular serine.

(7) Substrate Selectivity of Asc-2 (Inhibition Test Using Added Amino Acids and their Analogues)

In a serine uptake test in an oocyte into which a cRNA of the gene of the fusion protein of the Asc-2 with the rBAT (Asc-2-rBAT) was injected, the effect of amino acids and their analogues on the system was investigated.

The serine uptake test was conducted using the oocyte into which a cRNA of the gene of the fusion protein of the Asc-2 with the rBAT (Asc-2-rBAT) was injected in accordance with the method in Section (2) in Example 2 described above. Nevertheless, the test was conducted using as a sodium-free uptake solution (Na$^+$-free uptake solution), and the $^{14}$C-serine (5 µM) uptake was measured in the presence or absence of various compounds (non-labeled) at 500 µM.

Figure 13:
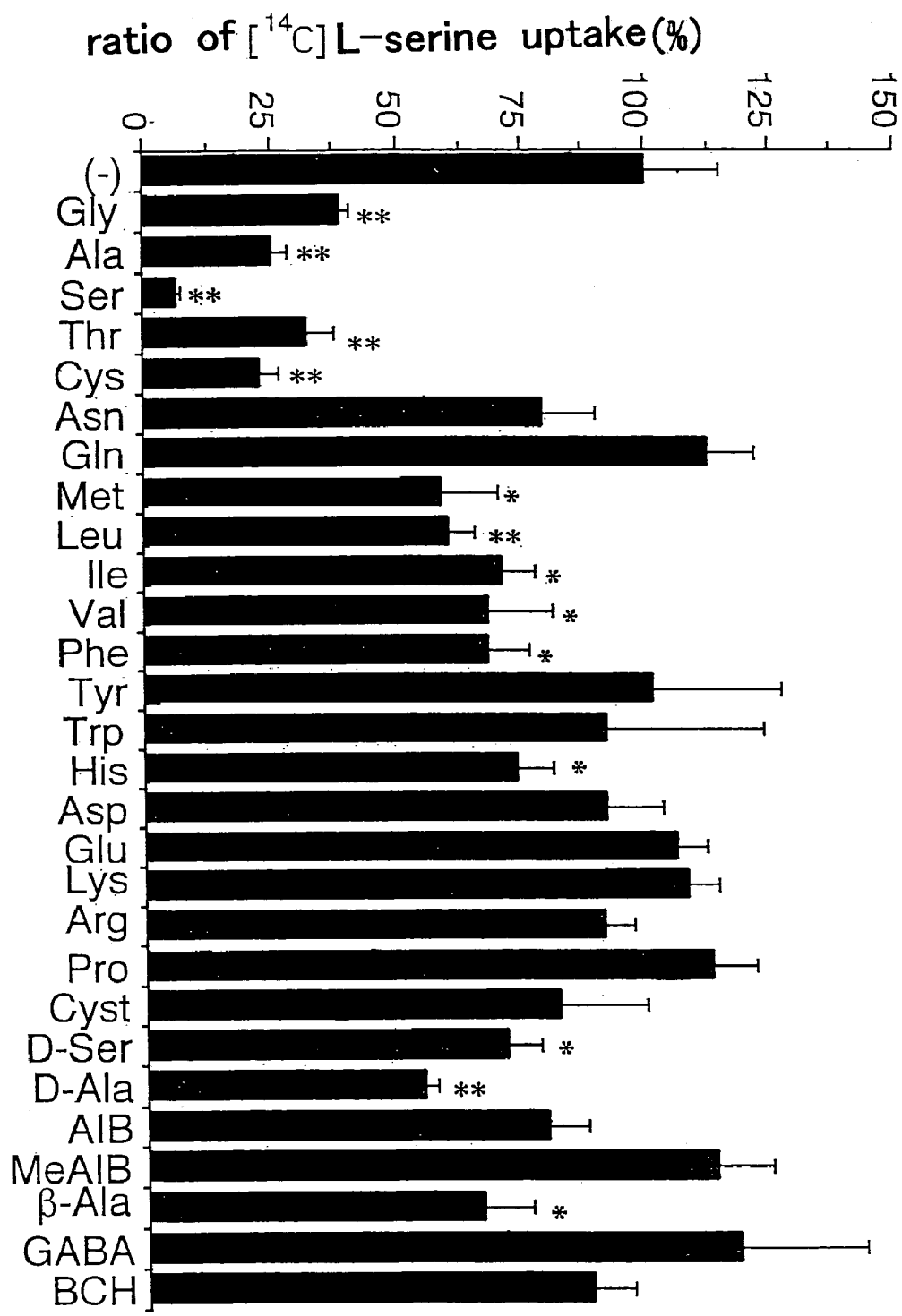
FIG. 13 shows the results of the investigation of the effects of the addition of various L-amino acids or their analogues to the system in the experiment of the serine uptake by the oocyte into which the cRNA of the gene of the fusion protein of the Asc-2 and the rBAT (Asc-2-rBAT) was injected.

The results are shown in FIG. 13. Various neutral L-amino acid exhibited a cis-inhibitory effect. Especially glycine, alanine, serine, threonine and cysteine inhibited potently the uptake of the Asc-2-rBAT-mediated $^{14}$C-serine.

Acidic amino acids, basic amino acids, transport system L-specific inhibitor 2-amino-2-norbornane-carboxylic acid (BCH), γ-aminoisoyric acid and α-aminoisometylic acid exhibited no effect on the Asc-2-rBAT-mediated $^{14}$C-serine uptake (FIG. 13).

similarly to the Asc-2-rBAT, in a serine uptake test in an oocyte into which a cRNA of the gene of the fusion protein of the Asc-2 with the 4F2hc (Asc-2-4F2hc) was injected together, the effect of amino acids and their analogues on the system was also investigated in the serine uptake test in the oocyte.

As a result, the Asc-2-4F2hc exhibited the behavior similar to that of the Asc-2-rBAT, and the part of the 4F2hc or the rBAT had no effect on the characteristics of the substrate-binding site of the fusion protein of the Asc-2 with the 4F2hc or rBAT (Asc-2-4F2hc or Asc-2-rBAT), and the data of the substrate selectivity obtained using the fusion proteins reflected the transport characteristics of the Asc-2 itself.

(8) Substrate Selectivity of Asc-2 (Uptake Test Using Various Amino Acids and their Analogues as Substrates)

Using various amino acids and their analogues as substrates, the uptake by an oocyte into which a cRNA of the gene of the fusion protein of the Asc-2 with the rBAT (Asc-2-rBAT) had been injected was investigated.

The uptake test of various amino acids and their analogues was conducted using the oocyte into which a cRNA of the gene of the fusion protein of the Asc-2 with the rBAT (Asc-2-rBAT) had been injected in accordance with the method in Section (2) in Example 2 described above. Nevertheless, the test was conducted using as a substrate various compounds which were radiolabeled instead of $^{14}$C-serine.

Figure 14:
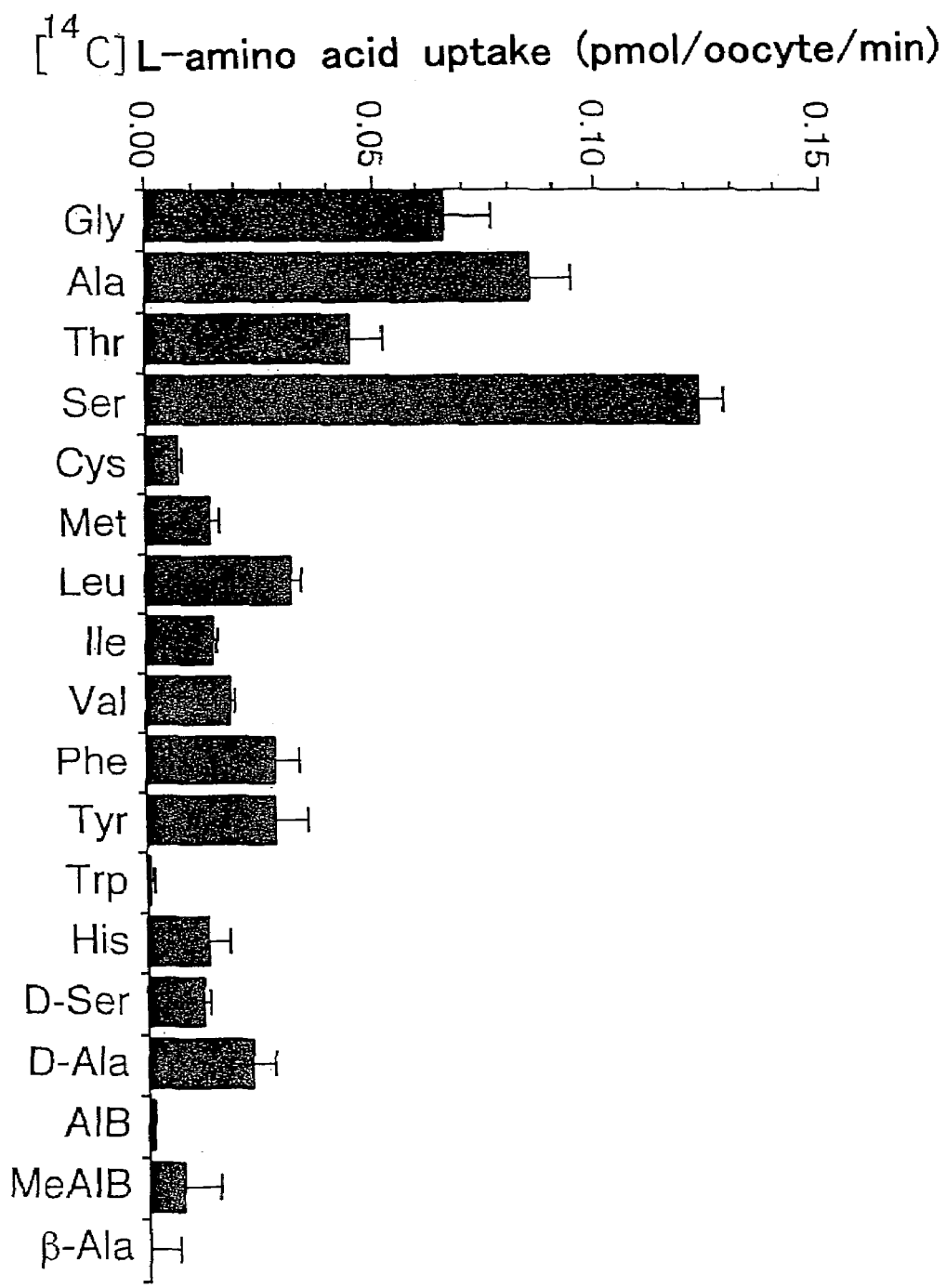
FIG. 14 shows the results of the radiolabeled amino acid uptake by the oocyte into which the cRNA of the gene of the fusion protein of the Asc-2 and the rBAT (Asc-2-rBAT) was injected. AIB means α-aminoisobutyric acid and MeAIB means α-methylaminoisobutyric acid. The ordinate indicates the serine uptake (pmol/oocyte/min).

The results are shown in FIG. 14. A substantial uptake into the oocyte was observed when using each of glycine ($^{14}$C compound), L-alanine ($^{14}$C compound), L-serine ($^{14}$C compound) and L-threonine ($^{14}$C compound) (all in FIG. 14) as a substrate.

Example 3

Immunohistochemical Analysis of Asc-2 Protein in Mouse Kidney

According to an ordinary method, a paraffin-embedded section of a mouse kidney was treated with an affinity-purified anti-Asc-2 antibody (1:100) and then stained with diaminobenzidine. In order to investigate the specificity of the staining, the treatment with the anti-AGT1 antiserum (1:100) in the presence of 200 µg/ml antigen peptide was also conducted.

Figure 15:
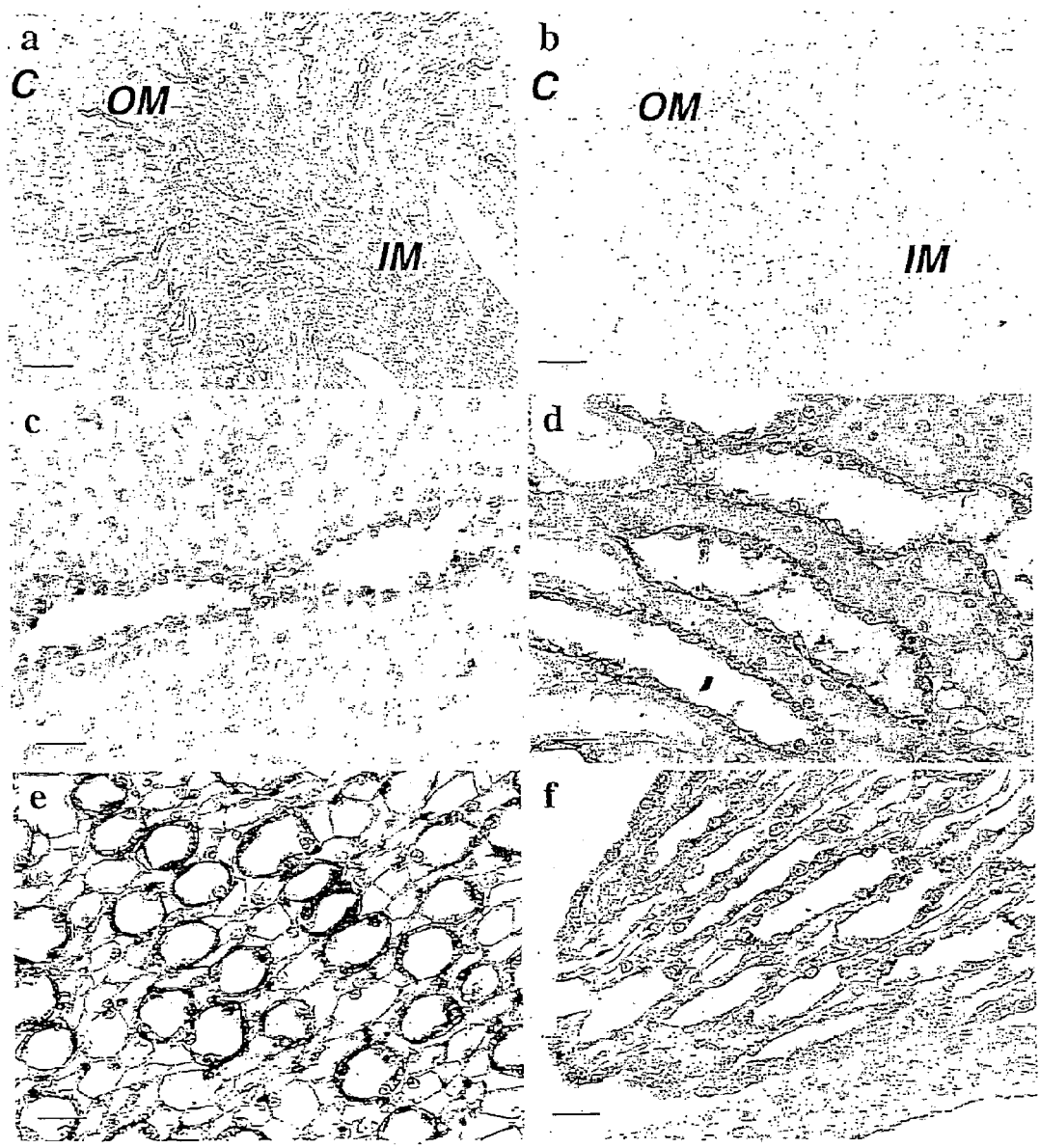
FIG. 15 is a photograph substituted for the drawing showing the results of the immunohistological analysis of the Asc-2 using an anti-Asc-2 antibody in a mouse kidney. The photo a shows a slightly magnified image. An intense staining was observed in a collecting tubule in the area from the outer layer to the inner layer of a medulla. The photo b shows the results of the absorption test using an antigen peptide. The staining observed in the photo a was disappeared, and the specificity of the staining was observed. The photo c is a highly magnified image of the cortical collecting tubule. The staining of the epithelium of the collecting tubule was noted. The photo d is a highly magnified image of the collecting tubule of the outer layer of the medulla. Luminal and basal membranes of the epithelium of the collecting tubule were stained. The photos e and f are highly magnified images of the collecting tubule of the inner layer of the medulla. Luminal and basal membranes of the epithelium of the collecting tubule were stained.

As a result, an intense staining was observed in a collecting tubule in the area from the outer layer to the inner layer of a medulla in the mouse kidney as shown in FIG. 15a. This staining was not observed when using the anti-Asc-2 antiserum in the presence of the antigen peptide, thus validating the specificity of the staining (FIG. 15b). A microscopic observation at a further higher magnification revealed that the Asc-2 protein existed in the cortical collecting tubule (FIG. 15c) and the collecting tubule of the outer layer of the medulla (FIG. 15d) as well as in the luminal and basal membranes of the collecting tubule of the inner layer of the medulla (FIGS. 15e and f).

INDUSTRIAL APPLICABILITY

An inventive sodium-independent transporter transporting small-sized neutral amino acid and its gene enables an in vitro investigation of the transport of the small-sized neutral amino acids and amino acid analogous including xenobiotics at the site where said transporter is expressed, and based on which, an in vitro assumption of the pharmacokinetics of these compounds is also enabled. Furthermore, the invention is useful in developing a pharmaceutical which permeates efficiently through a site where said transporter is expressed. Also by modulating an ability to transport a small-sized neutral amino acid and its analogue possessed by said transporter, the invention can be utilized in developing a method for controlling a cell proliferation. A method for analyzing a function of a transporter by constructing fused protein of the invention is a technology which enables the analysis of the function of a protein whose function can not be identified because of the inability to be transferred to a cell membrane since its cofactor required for the transfer to the cell membrane is unknown, and thus is useful in identifying the functions of various transporters whose functions have not been identified.

The invention claimed is:

1. An isolated protein consisting of the amino acid sequence represented by SEQ ID NO: 1.

2. An isolated fusion protein consisting of the amino acid sequence represented by SEQ ID NO: 1 and a protein having the amino acid sequence represented by SEQ ID NO: 3.

3. An isolated fusion protein consisting of the amino acid sequence represented by SEQ ID NO: 1 and a protein having the amino acid sequence represented by SEQ ID NO: 5.

4. An isolated DNA encoding a protein consisting of the amino acid sequence represented by SEQ ID NO: 1.

5. The isolated DNA according to claim 4 which consists of the base sequence represented by SEQ ID NO: 2.

6. An isolated DNA encoding a fusion protein consisting of the amino acid sequence represented by SEQ ID NO: 1 and a protein having the amino acid sequence represented by SEQ ID NO: 3.

7. An isolated DNA encoding a fusion protein consisting of the amino acid sequence represented by SEQ ID NO: 1 and a protein having the amino acid sequence represented by SEQ ID NO: 5.

8. A vector comprising the DNA defined in any one of claims 4 to 7.

9. The vector according to claim 8 which is an expression vector.

10. A transformant which has been transformed with a vector according to claim 8.

11. A method for identifying a substance which modulates an ability to transport a small-sized neutral amino acid in a sodium-independent manner possessed by a protein consisting of the amino acid sequence represented by SEQ ID NO: 1, which comprises a) providing a cell expressing the protein consisting of the amino acid sequence represented by SEQ ID NO: 1, b) incubating the substance and the small-sized neutral amino acid with the cell and c) determining an uptake of the small-sized neutral amino acid by the cell.

12. An isolated nucleic acid comprising a partial sequence of consecutive 14 bases or more in the base sequence represented by SEQ ID NO: 2 or a sequence complementary thereto.

* * * * *

SEQUENCE LISTING

```
<160> NUMBER OF SEQ ID NOS: 6

<210> SEQ ID NO 1
<211> LENGTH: 465
<212> TYPE: PRT
<213> ORGANISM: mouse

<400> SEQUENCE: 1

Met Gln Leu Leu Arg Ala Leu Gly Val Phe His Val Ser Met Ile Leu
 1               5                  10                  15
```

-continued

```
Phe Ser Ala Thr Leu Gly Thr Gly Ile Phe Val Thr Pro Lys Ala Val
             20                  25                  30
Leu Lys Tyr Ser Ser Leu Asn Ile Pro Val Ser Leu Ser Ile Trp Ala
             35                  40                  45
Gly Cys Gly Leu Leu Ser Ile Met Ser Ala Leu Cys Asn Ala Glu Ile
 50                  55                  60
Ala Thr Thr Tyr Pro Leu Ser Gly Ala Ser Tyr Tyr Phe Leu Lys Arg
 65                  70                  75                  80
Thr Leu Gly Ser Ser Val Ala Phe Leu Ser Leu Trp Ile Lys Leu Phe
             85                  90                  95
Ala His Phe Leu Gly Ile Gly Ala Gln Cys Leu Leu Ile Ala Thr Ser
             100                 105                 110
Val Ile Gln Cys Phe Tyr Ser Gly Cys Pro Ala Pro Glu Leu Pro Thr
             115                 120                 125
Lys Cys Leu Ala Leu Ala Ile Leu Trp Ser Phe Gly Ile Val Ser Ala
 130                 135                 140
Arg Gly Ile Lys Thr Val Ala Trp Phe Asn Thr Val Ser Ser Phe Ile
145                 150                 155                 160
Lys Leu Ser Val Leu Cys Leu Ile Ser Leu Thr Val Leu Leu Val Asn
             165                 170                 175
Gly Lys Lys Glu Asn Val Ser Arg Phe Glu Asn Ala Leu Asp Ala Glu
             180                 185                 190
Leu Pro Asn Ala Ser Gln Ile Ala Asp Ala Ile Leu Gln Val Ser Tyr
             195                 200                 205
Ser Tyr Leu Gly Ser Ser Val Leu Ile Val Ile Ala Gly Glu Ile Lys
             210                 215                 220
Arg Pro Thr Glu Thr Ile Pro Lys Thr Leu Ile Tyr Gly Ile Ser Ile
225                 230                 235                 240
Val Thr Val Leu Tyr Leu Leu Thr Asn Ile Ser Tyr Leu Ala Val Leu
             245                 250                 255
Thr Ser Gln Glu Ile Ile Phe Ser Asp Ser Val Gly Val Thr Trp Met
             260                 265                 270
Asn Arg Val Phe Pro Ser Ile Gln Trp Ile Ser Ser Phe Leu Ile Ser
             275                 280                 285
Ala Phe Leu Leu Gly Ser Val Ser Cys Gly Ile Val Ser Ala Ser Arg
 290                 295                 300
Val Phe Tyr Ser Ala Ser Gln Glu Gly Glu Phe Pro Ser Ile Tyr Ser
305                 310                 315                 320
Met Leu Asn Asp His His Ser Pro Ala Val Ala Asp Ile Gln Ile Val
             325                 330                 335
Ile Leu Ser Ser Val Ala Ile Ile Ser Ser Ile Ile Tyr Leu Val
             340                 345                 350
Lys Tyr Val Ser Leu Gly Ser Phe Cys Ile Asn Leu Leu Gln Met Ile
             355                 360                 365
Gly Leu Leu Lys Ile Arg Tyr Gln Asn Pro Asp Ile Pro Arg Pro Tyr
 370                 375                 380
Lys Val Trp Leu Pro Phe Ile Phe Gly Ser Ile Ala Leu Ser Leu Phe
385                 390                 395                 400
Leu Ile Phe Thr Pro Val Ile Gln Ser Pro Ser Ile Glu His Val Tyr
             405                 410                 415
Gln Val Val Phe Leu Phe Cys Gly Phe Leu Cys Tyr Trp Leu Gln Ala
             420                 425                 430
Asn Leu Asn Gly His Ala Thr Cys Phe Asp Thr Ile Thr Cys Tyr Cys
```

```
                     435                 440                 445
Gln Leu Leu Phe Asn Ile Ser Pro Ser Glu Asp Pro Glu Glu Gln Lys
    450                 455                 460

Asn
465

<210> SEQ ID NO 2
<211> LENGTH: 1759
<212> TYPE: DNA
<213> ORGANISM: mouse
<220> FEATURE:
<221> NAME/KEY: CDS
<222> LOCATION: (116)..(1513)
<223> OTHER INFORMATION: Asc-2
<300> PUBLICATION INFORMATION:

<400> SEQUENCE: 2
gcctgttggc ctactggaac accctgtttg acagggtttt tcacaaactg acagaaaagc        60
accataaaga aaaactgtat ttttcagtat ttgaaagagc aaaaaaggca taacc atg       118
                                                                  Met
                                                                    1 caa ctc ttg aga gca cta gga gtc ttc cat gta agc atg atc tta ttt        166
Gln Leu Leu Arg Ala Leu Gly Val Phe His Val Ser Met Ile Leu Phe
          5                  10                  15 agt gcc acc ctg ggg aca ggg att ttt gtg act cct aaa gca gta tta        214
Ser Ala Thr Leu Gly Thr Gly Ile Phe Val Thr Pro Lys Ala Val Leu
     20                  25                  30 aaa tac tcc tca cta aat atc cct gtc tcc tta agt att tgg gca ggc        262
Lys Tyr Ser Ser Leu Asn Ile Pro Val Ser Leu Ser Ile Trp Ala Gly
 35                  40                  45 tgc ggc ctg ctg agc atc atg agt gcg ctc tgt aat gca gag ata gca        310
Cys Gly Leu Leu Ser Ile Met Ser Ala Leu Cys Asn Ala Glu Ile Ala
 50                  55                  60                  65 acc acc tac cct ttg agt gga gca tct tat tat ttc ctc aag aga act        358
Thr Thr Tyr Pro Leu Ser Gly Ala Ser Tyr Tyr Phe Leu Lys Arg Thr
             70                  75                  80 ctt gga tcc tct gtt gct ttt ctc agt ctc tgg att aaa ctt ttt gct        406
Leu Gly Ser Ser Val Ala Phe Leu Ser Leu Trp Ile Lys Leu Phe Ala
             85                  90                  95 cac ttt cta ggc att ggt gct cag tgc ttg cta ata gct act tct gta        454
His Phe Leu Gly Ile Gly Ala Gln Cys Leu Leu Ile Ala Thr Ser Val
            100                 105                 110 atc cag tgt ttc tat tct ggg tgc cca gct cca gag cta cca acg aaa        502
Ile Gln Cys Phe Tyr Ser Gly Cys Pro Ala Pro Glu Leu Pro Thr Lys
        115                 120                 125 tgt ctg gct ttg gct att ttg tgg tca ttt gga att gtc agt gct cga        550
Cys Leu Ala Leu Ala Ile Leu Trp Ser Phe Gly Ile Val Ser Ala Arg
130                 135                 140                 145 ggg ata aaa aca gtg gct tgg ttt aat act gtc agc agt ttc atc aag        598
Gly Ile Lys Thr Val Ala Trp Phe Asn Thr Val Ser Ser Phe Ile Lys
                150                 155                 160 ttg agt gtc ctt tgt ctc att tct cta act gtg ctg tta gtg aat ggc        646
Leu Ser Val Leu Cys Leu Ile Ser Leu Thr Val Leu Leu Val Asn Gly
            165                 170                 175 aaa aag gag aat gtg tcc agg ttt gag aat gct ttg gat gct gaa ctt        694
Lys Lys Glu Asn Val Ser Arg Phe Glu Asn Ala Leu Asp Ala Glu Leu
            180                 185                 190 cct aat gcc tca cag atc gca gat gcc att ctc caa gtg tcc tac tca        742
Pro Asn Ala Ser Gln Ile Ala Asp Ala Ile Leu Gln Val Ser Tyr Ser
        195                 200                 205
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tat | cta | gga | tca | tca | gtc | ctc | atc | gtc | ata | gca | gga | gaa | ata | aaa | cgg | 790  |
| Tyr | Leu | Gly | Ser | Ser | Val | Leu | Ile | Val | Ile | Ala | Gly | Glu | Ile | Lys | Arg |      |
| 210 |     |     |     |     | 215 |     |     |     |     | 220 |     |     |     |     | 225 |      |

```
cca act gaa aca att cca aaa aca cta att tat ggt ata tcc att gtg    838
Pro Thr Glu Thr Ile Pro Lys Thr Leu Ile Tyr Gly Ile Ser Ile Val
                230                 235                 240 act gtg tta tac tta ctg act aat ata tca tac ttg gca gtt ttg aca    886
Thr Val Leu Tyr Leu Leu Thr Asn Ile Ser Tyr Leu Ala Val Leu Thr
            245                 250                 255 tcc cag gaa atc atc ttt tca gat tct gtt ggt gtc aca tgg atg aac    934
Ser Gln Glu Ile Ile Phe Ser Asp Ser Val Gly Val Thr Trp Met Asn
        260                 265                 270 aga gtc ttt cct tcc ata caa tgg ata agt tca ttc ttg atc tca gct    982
Arg Val Phe Pro Ser Ile Gln Trp Ile Ser Ser Phe Leu Ile Ser Ala
    275                 280                 285 ttc cta ctt ggc tcc gtt tct tgt gga ata gtt tct gca tca aga gta    1030
Phe Leu Leu Gly Ser Val Ser Cys Gly Ile Val Ser Ala Ser Arg Val
290                 295                 300                 305 ttc tac tct gca agt caa gag gga gaa ttt cct tct atc tac tca atg    1078
Phe Tyr Ser Ala Ser Gln Glu Gly Glu Phe Pro Ser Ile Tyr Ser Met
                310                 315                 320 ctt aat gat cat cac tca cca gct gta gct gac atc cag att gtt att    1126
Leu Asn Asp His His Ser Pro Ala Val Ala Asp Ile Gln Ile Val Ile
            325                 330                 335 tta tct tct gtt gca ata ata tct tca agt atc atc tat tta gtg aaa    1174
Leu Ser Ser Val Ala Ile Ile Ser Ser Ser Ile Ile Tyr Leu Val Lys
        340                 345                 350 tat gtt agt cta gga tca ttt tgt ata aat ttg ctg caa atg atc ggg    1222
Tyr Val Ser Leu Gly Ser Phe Cys Ile Asn Leu Leu Gln Met Ile Gly
    355                 360                 365 ttg ctt aag ata agg tac cag aac cct gat ata cca aga cct tat aag    1270
Leu Leu Lys Ile Arg Tyr Gln Asn Pro Asp Ile Pro Arg Pro Tyr Lys
370                 375                 380                 385 gtg tgg ctg cca ttt ata ttt gga tct ata gct tta tca ctt ttc ctc    1318
Val Trp Leu Pro Phe Ile Phe Gly Ser Ile Ala Leu Ser Leu Phe Leu
                390                 395                 400 att ttc aca cca gtg att cag tct cct agt ata gag cat gtc tat caa    1366
Ile Phe Thr Pro Val Ile Gln Ser Pro Ser Ile Glu His Val Tyr Gln
            405                 410                 415 gtt gtg ttt ctt ttt tgt ggg ttt ctg tgt tat tgg ctt caa gct aac    1414
Val Val Phe Leu Phe Cys Gly Phe Leu Cys Tyr Trp Leu Gln Ala Asn
        420                 425                 430 ctt aat gga cat gct act tgt ttt gac aca atc act tgc tac tgc caa    1462
Leu Asn Gly His Ala Thr Cys Phe Asp Thr Ile Thr Cys Tyr Cys Gln
    435                 440                 445 tta ctt ttc aat atc tcc cca tct gaa gat cca gaa gaa cag aaa aat    1510
Leu Leu Phe Asn Ile Ser Pro Ser Glu Asp Pro Glu Glu Gln Lys Asn
450                 455                 460                 465 taa ttccttctcc aaatcctgac taaagaagta tatttgaaaa gaaagaagca          1563
aaactatttt taaatgagca aaatttatt gcaattttat ttttagatat atgctttta    1623 acatgcttgc tcacattatt cccacccaaa aaaaaaatgt tgcaaatttt caattccacc  1683
tcataaacat ctttattcta tgaataatta gtagaaataa gattaaaggt aaaaaacaca  1743
aaaaaaaaaa aaaaaa                                                  1759
```

<210> SEQ ID NO 3
<211> LENGTH: 526
<212> TYPE: PRT
<213> ORGANISM: mouse

<400> SEQUENCE: 3

```
Met Ser Gln Asp Thr Glu Val Asp Met Lys Asp Val Glu Leu Asn Glu
  1               5                  10                  15
Leu Glu Pro Glu Lys Gln Pro Met Asn Ala Ala Asp Gly Ala Ala Ala
             20                  25                  30
Gly Glu Lys Asn Gly Leu Val Lys Ile Lys Val Ala Glu Asp Glu Thr
         35                  40                  45
Glu Ala Gly Val Lys Phe Thr Gly Leu Ser Lys Glu Glu Leu Leu Lys
     50                  55                  60
Val Ala Gly Ser Pro Gly Trp Val Arg Thr Arg Trp Ala Leu Leu Leu
 65                  70                  75                  80
Leu Phe Trp Leu Gly Trp Leu Gly Met Leu Ala Gly Ala Val Val Ile
                 85                  90                  95
Ile Val Arg Ala Pro Arg Cys Arg Glu Leu Pro Val Gln Arg Trp Trp
             100                 105                 110
His Lys Gly Ala Leu Tyr Arg Ile Gly Asp Leu Gln Ala Phe Val Gly
         115                 120                 125
Arg Asp Ala Gly Gly Ile Ala Gly Leu Lys Ser His Leu Glu Tyr Leu
     130                 135                 140
Ser Thr Leu Lys Val Lys Gly Leu Val Leu Gly Pro Ile His Lys Asn
145                 150                 155                 160
Gln Lys Asp Glu Ile Asn Glu Thr Asp Leu Lys Gln Ile Asn Pro Thr
                 165                 170                 175
Leu Gly Ser Gln Glu Asp Phe Lys Asp Leu Leu Gln Ser Ala Lys Lys
             180                 185                 190
Lys Ser Ile His Ile Ile Leu Asp Leu Thr Pro Asn Tyr Gln Gly Gln
         195                 200                 205
Asn Ala Trp Phe Leu Pro Ala Gln Ala Asp Ile Val Ala Thr Lys Met
     210                 215                 220
Lys Glu Ala Leu Ser Ser Trp Leu Gln Asp Gly Val Asp Gly Phe Gln
225                 230                 235                 240
Phe Arg Asp Val Gly Lys Leu Met Asn Ala Pro Leu Tyr Leu Ala Glu
                 245                 250                 255
Trp Gln Asn Ile Thr Lys Asn Leu Ser Glu Asp Arg Leu Leu Ile Ala
             260                 265                 270
Gly Thr Glu Ser Ser Asp Leu Gln Gln Ile Val Asn Ile Leu Glu Ser
         275                 280                 285
Thr Ser Asp Leu Leu Leu Thr Ser Ser Tyr Leu Ser Asn Ser Thr Phe
     290                 295                 300
Thr Gly Glu Arg Thr Glu Ser Leu Val Thr Arg Phe Leu Asn Ala Thr
305                 310                 315                 320
Gly Ser Gln Trp Cys Ser Trp Ser Val Ser Gln Ala Gly Leu Leu Ala
                 325                 330                 335
Asp Phe Ile Pro Asp His Leu Leu Arg Leu Tyr Gln Leu Leu Leu Phe
             340                 345                 350
Thr Leu Pro Gly Thr Pro Val Phe Ser Tyr Gly Asp Glu Leu Gly Leu
         355                 360                 365
Gln Gly Ala Leu Pro Gly Gln Pro Ala Lys Ala Pro Leu Met Pro Trp
     370                 375                 380
Asn Glu Ser Ser Ile Phe His Ile Pro Arg Pro Val Ser Leu Asn Met
385                 390                 395                 400
Thr Val Lys Gly Gln Asn Glu Asp Pro Gly Ser Leu Leu Thr Gln Phe
```

-continued

```
                        405                 410                 415
Arg Arg Leu Ser Asp Leu Arg Gly Lys Glu Arg Ser Leu Leu His Gly
                420                 425                 430
Asp Phe His Ala Leu Ser Ser Ser Pro Asp Leu Phe Ser Tyr Ile Arg
            435                 440                 445
His Trp Asp Gln Asn Glu Arg Tyr Leu Val Val Leu Asn Phe Arg Asp
        450                 455                 460
Ser Gly Arg Ser Ala Arg Leu Gly Ala Ser Asn Leu Pro Ala Gly Ile
465                 470                 475                 480
Ser Leu Pro Ala Ser Ala Lys Leu Leu Leu Ser Thr Asp Ser Ala Arg
                485                 490                 495
Gln Ser Arg Glu Glu Asp Thr Ser Leu Lys Leu Glu Asn Leu Ser Leu
                500                 505                 510
Asn Pro Tyr Glu Gly Leu Leu Leu Gln Phe Pro Phe Val Ala
                515                 520                 525

<210> SEQ ID NO 4
<211> LENGTH: 1852
<212> TYPE: DNA
<213> ORGANISM: mouse
<220> FEATURE:
<221> NAME/KEY: CDS
<222> LOCATION: (106)..(1686)
<223> OTHER INFORMATION: 4F2hc

<400> SEQUENCE: 4
gctagcctca cggccacggg acgcctctct gaacggggat ccaggcagga ttagagctgc      60
ctcactgact acaggccgtg tcgtgtcacc gtttctgcag gcacc atg agc cag gac     117
                                                  Met Ser Gln Asp
                                                    1 acc gaa gtg gac atg aaa gat gtg gag ctg aac gag cta gaa ccg gag     165
Thr Glu Val Asp Met Lys Asp Val Glu Leu Asn Glu Leu Glu Pro Glu
  5                  10                  15                  20 aag cag ccc atg aat gca gcg gac ggg gcg gcg gcc ggg gag aag aac     213
Lys Gln Pro Met Asn Ala Ala Asp Gly Ala Ala Ala Gly Glu Lys Asn
                 25                  30                  35 ggt ctg gtg aag atc aag gtg gcg gag gac gag acg gag gcc ggg gtc     261
Gly Leu Val Lys Ile Lys Val Ala Glu Asp Glu Thr Glu Ala Gly Val
             40                  45                  50 aag ttc acc ggc tta tcc aag gag gag cta ctg aag gta gcg ggc agc     309
Lys Phe Thr Gly Leu Ser Lys Glu Glu Leu Leu Lys Val Ala Gly Ser
         55                  60                  65 cct ggc tgg gtg cgc acc cgc tgg gcg ctg ctg ctc ttc tgg ctc         357
Pro Gly Trp Val Arg Thr Arg Trp Ala Leu Leu Leu Phe Trp Leu
     70                  75                  80 ggt tgg ctg ggc atg ctg gcg ggc gcc gtg gtt atc atc gtt cgg gcg     405
Gly Trp Leu Gly Met Leu Ala Gly Ala Val Val Ile Ile Val Arg Ala
 85                  90                  95                 100 ccg cgc tgc cgt gag ctg cct gta cag agg tgg tgg cac aag ggc gcc     453
Pro Arg Cys Arg Glu Leu Pro Val Gln Arg Trp Trp His Lys Gly Ala
                105                 110                 115 ctc tac cgc atc ggc gac ctt cag gcc ttt gta ggc cgg gat gcg gga     501
Leu Tyr Arg Ile Gly Asp Leu Gln Ala Phe Val Gly Arg Asp Ala Gly
            120                 125                 130 ggc ata gct ggt ctc aag agc cat ctg gag tac ttg agc acc ctg aag     549
Gly Ile Ala Gly Leu Lys Ser His Leu Glu Tyr Leu Ser Thr Leu Lys
        135                 140                 145 gtg aag ggc ctg gtg tta ggc cca att cac aag aac cag aag gat gaa     597
Val Lys Gly Leu Val Leu Gly Pro Ile His Lys Asn Gln Lys Asp Glu
```

```
                150                  155                  160
atc aat gaa acc gac ctg aaa cag att aat ccc act ttg ggc tcc cag        645
Ile Asn Glu Thr Asp Leu Lys Gln Ile Asn Pro Thr Leu Gly Ser Gln
165                 170                 175                 180 gaa gat ttt aaa gac ctt cta caa agt gcc aag aaa aag agc att cac        693
Glu Asp Phe Lys Asp Leu Leu Gln Ser Ala Lys Lys Lys Ser Ile His
                185                 190                 195 atc att ttg gac ctc act ccc aac tac cag ggc cag aat gcg tgg ttc        741
Ile Ile Leu Asp Leu Thr Pro Asn Tyr Gln Gly Gln Asn Ala Trp Phe
200                 205                 210 ctc cct gct cag gct gac att gta gcc acc aaa atg aag gaa gct ctg        789
Leu Pro Ala Gln Ala Asp Ile Val Ala Thr Lys Met Lys Glu Ala Leu
        215                 220                 225 agt tct tgg ttg cag gac ggt gtg gat ggt ttc caa ttc cgg gat gtg        837
Ser Ser Trp Leu Gln Asp Gly Val Asp Gly Phe Gln Phe Arg Asp Val
        230                 235                 240 gga aag ctg atg aat gca ccc ttg tac ttg gct gag tgg cag aat atc        885
Gly Lys Leu Met Asn Ala Pro Leu Tyr Leu Ala Glu Trp Gln Asn Ile
245                 250                 255                 260 acc aag aac tta agt gag gac agg ctt ttg att gca ggg act gag tcc        933
Thr Lys Asn Leu Ser Glu Asp Arg Leu Leu Ile Ala Gly Thr Glu Ser
                265                 270                 275 tct gac ctg cag caa att gtc aac ata ctt gaa tcc acc agc gac ctg        981
Ser Asp Leu Gln Gln Ile Val Asn Ile Leu Glu Ser Thr Ser Asp Leu
                280                 285                 290 ctg ttg acc agc tcc tac ctg tca aat tcc act ttc act ggg gag cgt       1029
Leu Leu Thr Ser Ser Tyr Leu Ser Asn Ser Thr Phe Thr Gly Glu Arg
        295                 300                 305 act gaa tcc cta gtc act agg ttt ttg aat gcc act ggc agc caa tgg       1077
Thr Glu Ser Leu Val Thr Arg Phe Leu Asn Ala Thr Gly Ser Gln Trp
310                 315                 320 tgc agc tgg agt gtg tcg caa gca gga ctc ctc gca gac ttt ata ccg       1125
Cys Ser Trp Ser Val Ser Gln Ala Gly Leu Leu Ala Asp Phe Ile Pro
325                 330                 335                 340 gac cat ctt ctc cga ctc tac cag ctg ctg ctc ttc act ctg cca ggg       1173
Asp His Leu Leu Arg Leu Tyr Gln Leu Leu Leu Phe Thr Leu Pro Gly
                345                 350                 355 act cct gtt ttt agc tac ggg gat gag ctt ggc ctt cag ggt gcc ctt       1221
Thr Pro Val Phe Ser Tyr Gly Asp Glu Leu Gly Leu Gln Gly Ala Leu
        360                 365                 370 cct gga cag cct gcg aag gcc cca ctc atg ccg tgg aat gag tcc agc       1269
Pro Gly Gln Pro Ala Lys Ala Pro Leu Met Pro Trp Asn Glu Ser Ser
        375                 380                 385 atc ttt cac atc cca aga cct gta agc ctc aac atg aca gtg aag ggc       1317
Ile Phe His Ile Pro Arg Pro Val Ser Leu Asn Met Thr Val Lys Gly
390                 395                 400 cag aat gaa gac cct ggc tcc ctt ctt acc cag ttc cgg cgg ctg agt       1365
Gln Asn Glu Asp Pro Gly Ser Leu Leu Thr Gln Phe Arg Arg Leu Ser
405                 410                 415                 420 gac ctt cgg ggt aag gag cgc tct ctg ttg cac ggt gac ttc cat gca       1413
Asp Leu Arg Gly Lys Glu Arg Ser Leu Leu His Gly Asp Phe His Ala
                425                 430                 435 ctg tct tcc tca cct gac ctc ttc tcc tac ata cga cac tgg gac cag       1461
Leu Ser Ser Ser Pro Asp Leu Phe Ser Tyr Ile Arg His Trp Asp Gln
                440                 445                 450 aat gag cgt tac ctg gtg gtg ctc aac ttc cga gat tcg ggc cgg tca       1509
Asn Glu Arg Tyr Leu Val Val Leu Asn Phe Arg Asp Ser Gly Arg Ser
        455                 460                 465 gcc agg cta ggg gcc tcc aac ctc cct gct ggc ata agc ctg cca gcc       1557
```

-continued

```
                Ala Arg Leu Gly Ala Ser Asn Leu Pro Ala Gly Ile Ser Leu Pro Ala
                    470                 475                 480 agc gct aaa ctt ttg ctt agt acc gac agt gcc cgg caa agc cgt gag        1605
Ser Ala Lys Leu Leu Leu Ser Thr Asp Ser Ala Arg Gln Ser Arg Glu
485                 490                 495                 500 gag gac acc tcc ctg aag ctg gaa aac ctg agc ctg aat cct tat gag        1653
Glu Asp Thr Ser Leu Lys Leu Glu Asn Leu Ser Leu Asn Pro Tyr Glu
                505                 510                 515 ggc ttg ctg tta cag ttc ccc ttt gtg gcc tga tccttcctat gcagaaccta     1706
Gly Leu Leu Leu Gln Phe Pro Phe Val Ala
                520                 525 ccaccctcct tgttctccc caggccttt ggattctagt cttcctctcc ttgtttttaa       1766
acttttgcag attacatacg aattcttata ctgggtgttt ttgtcttcaa ataaaaacat     1826 caccctgcc tcaaaaaaaa aaaaaa                                           1852
```

<210> SEQ ID NO 5
<211> LENGTH: 685
<212> TYPE: PRT
<213> ORGANISM: mouse

<400> SEQUENCE: 5

```
Met Asp Glu Asp Lys Gly Lys Arg Asp Pro Ile Gln Met Ser Met Lys
1               5                   10                  15

Gly Cys Arg Thr Asn Asn Gly Phe Val Gln Asn Glu Asp Ile Pro Glu
                20                  25                  30

Gln Asp Pro Asp Pro Gly Ser Arg Asp Thr Pro Gln Pro Asn Ala Val
            35                  40                  45

Ser Ile Pro Ala Pro Glu Glu Pro His Leu Lys Ala Val Arg Pro Tyr
    50                  55                  60

Ala Gly Met Pro Lys Glu Val Leu Phe Gln Phe Ser Gly Gln Ala Arg
65                  70                  75                  80

Tyr Arg Val Pro Arg Glu Ile Leu Phe Trp Leu Thr Val Ser Val
                85                  90                  95

Phe Leu Leu Ile Gly Ala Thr Ile Ala Ile Val Ile Ser Pro Lys
                100                 105                 110

Cys Leu Asp Trp Trp Gln Ala Gly Pro Ile Tyr Gln Ile Tyr Pro Arg
            115                 120                 125

Ser Phe Lys Asp Ser Asp Lys Asp Gly Asn Gly Asp Leu Lys Gly Ile
    130                 135                 140

Gln Glu Lys Leu Asp Tyr Ile Thr Ala Leu Asn Ile Lys Thr Leu Trp
145                 150                 155                 160

Ile Thr Ser Phe Tyr Lys Ser Ile Phe Glu Asp Phe Arg Tyr Ala Val
                165                 170                 175

Glu Asp Ile Lys Glu Ile Asp Pro Ile Phe Gly Thr Met Lys Asp Phe
            180                 185                 190

Glu Asn Leu Val Ala Ala Ile His Asp Lys Gly Leu Lys Leu Ile Ile
        195                 200                 205

Asp Phe Ile Pro Asn His Thr Ser Asp Lys His Pro Trp Phe Gln Ser
    210                 215                 220

Ser Arg Thr Arg Ser Gly Lys Tyr Thr Asp Tyr Tyr Ile Trp His Asn
225                 230                 235                 240

Cys Thr His Cys Gln Arg Val Pro Thr Pro Asn Asn Trp Leu Ser
                245                 250                 255

Val Tyr Gly His Ser Ser Trp His Phe Asp Glu Val Arg Glu Gln Cys
            260                 265                 270
```

```
Tyr Phe His Gln Phe Leu Arg Glu Gln Pro Asp Leu Tyr Phe Arg Asn
        275                 280                 285

Pro Ala Val Gln Glu Ile Lys Glu Ile Thr Phe Trp Leu Ser
    290                 295                 300

Lys Gly Val Asp Gly Phe Ser Phe Asp Ala Val Lys Phe Leu Leu Glu
305                 310                 315                 320

Ala Lys Asp Leu Arg Asn Glu Ile Gln Val Asn Thr Ser Gln Ile Pro
                325                 330                 335

Asp Thr Val Thr His Tyr Ser Glu Leu Tyr His Asp Phe Thr Thr Thr
            340                 345                 350

Gln Val Gly Met His Asp Ile Val Arg Asp Phe Arg Gln Thr Met Asn
        355                 360                 365

Gln Tyr Ser Arg Glu Pro Gly Arg Tyr Arg Phe Met Gly Ala Glu Ala
    370                 375                 380

Ser Ala Glu Ser Ile Glu Arg Thr Met Met Tyr Tyr Gly Leu Pro Phe
385                 390                 395                 400

Ile Gln Glu Ala Asp Phe Pro Phe Asn Lys Tyr Phe Thr Thr Ile Gly
                405                 410                 415

Thr Leu Ser Gly His Thr Val Tyr Glu Val Ile Thr Ser Trp Met Glu
            420                 425                 430

Asn Met Pro Glu Gly Lys Trp Pro Asn Trp Met Thr Gly Gly Pro Glu
        435                 440                 445

Thr Pro Arg Leu Thr Ser Arg Val Gly Ser Glu Tyr Val Asn Ala Met
    450                 455                 460

His Met Leu Leu Phe Thr Leu Pro Gly Thr Pro Ile Thr Tyr Tyr Gly
465                 470                 475                 480

Glu Glu Ile Gly Met Gly Asp Ile Ser Val Thr Asn Phe Asn Glu Ser
                485                 490                 495

Tyr Asp Ser Thr Thr Leu Val Ser Lys Ser Pro Met Gln Trp Asp Asn
            500                 505                 510

Ser Ser Asn Ala Gly Phe Thr Glu Ala Asn His Thr Trp Leu Pro Pro
        515                 520                 525

Asn Ser Asp Tyr His Thr Val Asn Val Asp Val Gln Lys Thr Gln Pro
    530                 535                 540

Ser Ser Ala Leu Arg Leu Tyr Gln Asp Leu Ser Leu Leu His Ala Thr
545                 550                 555                 560

Glu Leu Val Leu Ser Arg Gly Trp Phe Cys Leu Leu Arg Asp Asp Ser
                565                 570                 575

His Ser Val Val Tyr Thr Arg Glu Leu Asp Gly Ile Asp Asn Val Phe
            580                 585                 590

Leu Val Val Leu Asn Phe Gly Glu Ser Ser Thr Val Leu Asn Leu Gln
        595                 600                 605

Gly Ile Ile Ser Asp Leu Pro Pro Glu Leu Arg Ile Arg Leu Ser Thr
    610                 615                 620

Asn Ser Ala Ser Lys Gly Ser Ala Val Asp Thr Arg Ala Ile Ser Leu
625                 630                 635                 640

Glu Lys Gly Glu Gly Leu Val Leu Glu His Ser Thr Lys Ala Pro Leu
                645                 650                 655

His Gln Gln Ala Ala Phe Arg Asp Arg Cys Phe Val Ser Ser Arg Ala
            660                 665                 670

Cys Tyr Ser Ser Ala Leu Asp Ile Leu Tyr Ser Ser Cys
        675                 680                 685
```

-continued

```
<210> SEQ ID NO 6
<211> LENGTH: 2287
<212> TYPE: DNA
<213> ORGANISM: mouse
<220> FEATURE:
<221> NAME/KEY: CDS
<222> LOCATION: (46)..(2103)
<223> OTHER INFORMATION: rBAT

<400> SEQUENCE: 6
```

| | | | | | | | | | | | | |
|---|---|---|---|---|---|---|---|---|---|---|---|---|
| gatcccctg ctggaaagca ccaggaagag ctacacaggg tagac atg gat gag gac | | | | | | | | | | | | 57 |
| | | | | | | | | | Met | Asp | Glu | Asp |
| | | | | | | | | | 1 | | | |

| aaa | ggc | aag | aga | gac | ccc | atc | caa | atg | agt | atg | aag | gga | tgc | cga | acc | 105 |
|---|---|---|---|---|---|---|---|---|---|---|---|---|---|---|---|---|
| Lys | Gly | Lys | Arg | Asp | Pro | Ile | Gln | Met | Ser | Met | Lys | Gly | Cys | Arg | Thr | |
| 5 | | | | 10 | | | | | 15 | | | | | | 20 | |

| aat | aac | ggg | ttt | gtc | caa | aat | gaa | gac | att | ccg | gag | cag | gac | cca | gac | 153 |
|---|---|---|---|---|---|---|---|---|---|---|---|---|---|---|---|---|
| Asn | Asn | Gly | Phe | Val | Gln | Asn | Glu | Asp | Ile | Pro | Glu | Gln | Asp | Pro | Asp | |
| | 25 | | | | | 30 | | | | | 35 | | | | | |

| cca | ggc | tcc | agg | gac | acc | cca | cag | ccc | aac | gcc | gtg | agt | atc | cct | gct | 201 |
|---|---|---|---|---|---|---|---|---|---|---|---|---|---|---|---|---|
| Pro | Gly | Ser | Arg | Asp | Thr | Pro | Gln | Pro | Asn | Ala | Val | Ser | Ile | Pro | Ala | |
| | | 40 | | | | | 45 | | | | | 50 | | | | |

| cca | gag | gag | cct | cac | cta | aag | gcg | gtg | cgg | ccc | tat | gca | ggg | atg | ccc | 249 |
|---|---|---|---|---|---|---|---|---|---|---|---|---|---|---|---|---|
| Pro | Glu | Glu | Pro | His | Leu | Lys | Ala | Val | Arg | Pro | Tyr | Ala | Gly | Met | Pro | |
| 55 | | | | | 60 | | | | | 65 | | | | | | |

| aag | gaa | gta | ctc | ttc | cag | ttc | tcc | ggc | cag | gct | cgc | tac | cgg | gtg | ccc | 297 |
|---|---|---|---|---|---|---|---|---|---|---|---|---|---|---|---|---|
| Lys | Glu | Val | Leu | Phe | Gln | Phe | Ser | Gly | Gln | Ala | Arg | Tyr | Arg | Val | Pro | |
| 70 | | | | | 75 | | | | | 80 | | | | | | |

| cga | gag | atc | ctc | ttc | tgg | ctc | acc | gtg | gtt | tcc | gtg | ttc | ctg | ctc | att | 345 |
|---|---|---|---|---|---|---|---|---|---|---|---|---|---|---|---|---|
| Arg | Glu | Ile | Leu | Phe | Trp | Leu | Thr | Val | Val | Ser | Val | Phe | Leu | Leu | Ile | |
| 85 | | | | | 90 | | | | | 95 | | | | | 100 | |

| gga | gcc | acc | ata | gcc | atc | atc | gtc | atc | tct | cca | aaa | tgc | ctt | gac | tgg | 393 |
|---|---|---|---|---|---|---|---|---|---|---|---|---|---|---|---|---|
| Gly | Ala | Thr | Ile | Ala | Ile | Ile | Val | Ile | Ser | Pro | Lys | Cys | Leu | Asp | Trp | |
| | | | | 105 | | | | | 110 | | | | | 115 | | |

| tgg | caa | gca | ggt | ccc | ata | tac | cag | atc | tac | ccg | agg | tct | ttt | aag | gac | 441 |
|---|---|---|---|---|---|---|---|---|---|---|---|---|---|---|---|---|
| Trp | Gln | Ala | Gly | Pro | Ile | Tyr | Gln | Ile | Tyr | Pro | Arg | Ser | Phe | Lys | Asp | |
| | | | 120 | | | | | 125 | | | | | 130 | | | |

| agt | gac | aag | gat | ggg | aat | gga | gac | ctg | aaa | ggt | atc | cag | gag | aag | ctg | 489 |
|---|---|---|---|---|---|---|---|---|---|---|---|---|---|---|---|---|
| Ser | Asp | Lys | Asp | Gly | Asn | Gly | Asp | Leu | Lys | Gly | Ile | Gln | Glu | Lys | Leu | |
| | 135 | | | | | 140 | | | | | 145 | | | | | |

| gac | tat | atc | act | gct | tta | aac | ata | aag | act | ctt | tgg | atc | act | tcc | ttt | 537 |
|---|---|---|---|---|---|---|---|---|---|---|---|---|---|---|---|---|
| Asp | Tyr | Ile | Thr | Ala | Leu | Asn | Ile | Lys | Thr | Leu | Trp | Ile | Thr | Ser | Phe | |
| | 150 | | | | | 155 | | | | | 160 | | | | | |

| tat | aaa | tcg | atc | ttt | gaa | gac | ttc | aga | tac | gct | gtt | gag | gat | atc | aaa | 585 |
|---|---|---|---|---|---|---|---|---|---|---|---|---|---|---|---|---|
| Tyr | Lys | Ser | Ile | Phe | Glu | Asp | Phe | Arg | Tyr | Ala | Val | Glu | Asp | Ile | Lys | |
| 165 | | | | | 170 | | | | | 175 | | | | | 180 | |

| gaa | att | gac | cct | att | ttt | gga | aca | atg | aaa | gat | ttt | gag | aat | ttg | gtt | 633 |
|---|---|---|---|---|---|---|---|---|---|---|---|---|---|---|---|---|
| Glu | Ile | Asp | Pro | Ile | Phe | Gly | Thr | Met | Lys | Asp | Phe | Glu | Asn | Leu | Val | |
| | | | | 185 | | | | | 190 | | | | | 195 | | |

| gct | gcc | atc | cat | gac | aaa | ggt | tta | aaa | tta | ata | att | gat | ttc | ata | cca | 681 |
|---|---|---|---|---|---|---|---|---|---|---|---|---|---|---|---|---|
| Ala | Ala | Ile | His | Asp | Lys | Gly | Leu | Lys | Leu | Ile | Ile | Asp | Phe | Ile | Pro | |
| | | | 200 | | | | | 205 | | | | | 210 | | | |

| aac | cac | act | agt | gac | aaa | cat | cct | tgg | ttc | caa | tcg | agt | agg | aca | cgg | 729 |
|---|---|---|---|---|---|---|---|---|---|---|---|---|---|---|---|---|
| Asn | His | Thr | Ser | Asp | Lys | His | Pro | Trp | Phe | Gln | Ser | Ser | Arg | Thr | Arg | |
| | | 215 | | | | | 220 | | | | | 225 | | | | |

| agc | gga | aaa | tac | acc | gat | tac | tac | atc | tgg | cac | aac | tgt | acc | cat | tgt | 777 |
|---|---|---|---|---|---|---|---|---|---|---|---|---|---|---|---|---|
| Ser | Gly | Lys | Tyr | Thr | Asp | Tyr | Tyr | Ile | Trp | His | Asn | Cys | Thr | His | Cys | |
| | 230 | | | | | 235 | | | | | 240 | | | | | |

| caa | cgt | gta | ccc | acc | cct | ccc | aac | aac | tgg | ctg | agt | gtg | tat | gga | cac | 825 |
|---|---|---|---|---|---|---|---|---|---|---|---|---|---|---|---|---|
| Gln | Arg | Val | Pro | Thr | Pro | Pro | Asn | Asn | Trp | Leu | Ser | Val | Tyr | Gly | His | |
| 245 | | | | | 250 | | | | | 255 | | | | | 260 | |

| | | |
|---|---|---|
| tcc agc tgg cac ttt gat gaa gta cga gag caa tgt tat ttt cac cag<br>Ser Ser Trp His Phe Asp Glu Val Arg Glu Gln Cys Tyr Phe His Gln<br>265 270 275 | | 873 |
| ttt ttg aga gag caa cca gat tta tat ttc cga aat cct gct gtt caa<br>Phe Leu Arg Glu Gln Pro Asp Leu Tyr Phe Arg Asn Pro Ala Val Gln<br>280 285 290 | | 921 |
| gag gaa ata aag gaa ata ata acg ttc tgg ctc tcg aag ggt gtt gat<br>Glu Glu Ile Lys Glu Ile Ile Thr Phe Trp Leu Ser Lys Gly Val Asp<br>295 300 305 | | 969 |
| ggg ttt agt ttt gat gca gtt aaa ttt ctt ctg gaa gcg aag gat ctg<br>Gly Phe Ser Phe Asp Ala Val Lys Phe Leu Leu Glu Ala Lys Asp Leu<br>310 315 320 | | 1017 |
| aga aat gaa atc caa gtg aat aca tcc caa att ccg gac acg gtc acc<br>Arg Asn Glu Ile Gln Val Asn Thr Ser Gln Ile Pro Asp Thr Val Thr<br>325 330 335 340 | | 1065 |
| cac tac tca gag ctg tac cat gac ttc acc aca act cag gtg gga atg<br>His Tyr Ser Glu Leu Tyr His Asp Phe Thr Thr Thr Gln Val Gly Met<br>345 350 355 | | 1113 |
| cat gac atc gtc cga gac ttc cgg cag acc atg aac cag tac agc agg<br>His Asp Ile Val Arg Asp Phe Arg Gln Thr Met Asn Gln Tyr Ser Arg<br>360 365 370 | | 1161 |
| gag cct ggc aga tac cgg ttc atg ggg gcc gaa gcc tca gct gag agc<br>Glu Pro Gly Arg Tyr Arg Phe Met Gly Ala Glu Ala Ser Ala Glu Ser<br>375 380 385 | | 1209 |
| atc gag agg acc atg atg tac tat ggc ttg cca ttt atc cag gaa gcc<br>Ile Glu Arg Thr Met Met Tyr Tyr Gly Leu Pro Phe Ile Gln Glu Ala<br>390 395 400 | | 1257 |
| gac ttt cct ttc aac aag tac ttc acc aca ata ggc act ctc tct ggg<br>Asp Phe Pro Phe Asn Lys Tyr Phe Thr Thr Ile Gly Thr Leu Ser Gly<br>405 410 415 420 | | 1305 |
| cat act gtc tat gaa gtt atc aca tcc tgg atg gaa aac atg cct gaa<br>His Thr Val Tyr Glu Val Ile Thr Ser Trp Met Glu Asn Met Pro Glu<br>425 430 435 | | 1353 |
| gga aaa tgg ccc aat tgg atg act ggc gga ccg gag act cct cgg ctg<br>Gly Lys Trp Pro Asn Trp Met Thr Gly Gly Pro Glu Thr Pro Arg Leu<br>440 445 450 | | 1401 |
| act tct cga gta ggg agt gag tat gtc aac gcc atg cac atg ctc ctg<br>Thr Ser Arg Val Gly Ser Glu Tyr Val Asn Ala Met His Met Leu Leu<br>455 460 465 | | 1449 |
| ttc aca ctc ccg gga acg ccc atc act tac tat gga gag gaa atc ggg<br>Phe Thr Leu Pro Gly Thr Pro Ile Thr Tyr Tyr Gly Glu Glu Ile Gly<br>470 475 480 | | 1497 |
| atg gga gac att tcc gtt aca aat ttc aac gag agc tat gat agt act<br>Met Gly Asp Ile Ser Val Thr Asn Phe Asn Glu Ser Tyr Asp Ser Thr<br>485 490 495 500 | | 1545 |
| acc ctt gtc tcc aag tca ccg atg cag tgg gac aat agt tcc aat gct<br>Thr Leu Val Ser Lys Ser Pro Met Gln Trp Asp Asn Ser Ser Asn Ala<br>505 510 515 | | 1593 |
| ggg ttt act gag gcc aac cac acc tgg cta cca cca aac tct gac tac<br>Gly Phe Thr Glu Ala Asn His Thr Trp Leu Pro Pro Asn Ser Asp Tyr<br>520 525 530 | | 1641 |
| cac acc gtc aat gtg gat gtc caa aag acc cag ccg agc tcc gca ctg<br>His Thr Val Asn Val Asp Val Gln Lys Thr Gln Pro Ser Ser Ala Leu<br>535 540 545 | | 1689 |
| agg ctg tat cag gat ctg agt cta ctc cat gcc aca gag ctg gtc ctc<br>Arg Leu Tyr Gln Asp Leu Ser Leu Leu His Ala Thr Glu Leu Val Leu<br>550 555 560 | | 1737 |
| agc cgg ggc tgg ttt tgc ctc ttg aga gac gac agt cac tct gtg gtg<br>Ser Arg Gly Trp Phe Cys Leu Leu Arg Asp Asp Ser His Ser Val Val | | 1785 |

-continued

```
565                  570                  575                  580
tac aca aga gag ctg gac ggc ata gat aac gtc ttc ctc gtg gtt ctg     1833
Tyr Thr Arg Glu Leu Asp Gly Ile Asp Asn Val Phe Leu Val Val Leu
                585                      590                  595 aat ttt gga gaa tca tca act gtg cta aat cta cag ggg atc att tca     1881
Asn Phe Gly Glu Ser Ser Thr Val Leu Asn Leu Gln Gly Ile Ile Ser
                600                      605                  610 gat ctt cct cca gag ctg aga ata agg tta agt acc aac tca gcc tcc     1929
Asp Leu Pro Pro Glu Leu Arg Ile Arg Leu Ser Thr Asn Ser Ala Ser
                615                      620                  625 aaa ggc agt gct gtt gac acc cgt gcc att tct ctg gag aag gga gag     1977
Lys Gly Ser Ala Val Asp Thr Arg Ala Ile Ser Leu Glu Lys Gly Glu
                630                      635                  640 ggc ctg gtc ttg gag cac agc acg aag gct ccc ctc cat cag cag gcc     2025
Gly Leu Val Leu Glu His Ser Thr Lys Ala Pro Leu His Gln Gln Ala
645                  650                      655                  660 gct ttc aga gac aga tgc ttt gtt tcc agt cgg gcg tgc tac tcc agt     2073
Ala Phe Arg Asp Arg Cys Phe Val Ser Ser Arg Ala Cys Tyr Ser Ser
                    665                      670                  675 gca ctg gac atc ctc tat agc tcg tgt tag ggaggaagct ccctaagaga       2123
Ala Leu Asp Ile Leu Tyr Ser Ser Cys
                680                  685 tggccaccca gaacatcacg tacgcacagg ctgagcagac tcatgaatgg catcaattct   2183
tagatatttc tgtagcacga tgcacgtttt ttaaagtgtt taaagattat gccaaatact   2243
aaagcattta aatatgaaaa aaaaaaaaaa aaagcggcgc gccg                    2287
```